(12) United States Patent
Yang

(10) Patent No.: US 6,787,340 B2
(45) Date of Patent: Sep. 7, 2004

(54) APPARATUS FOR SEPARATING CELLS AND PRODUCING MICROBIAL POLYSACCHARIDES

(75) Inventor: Shang-Tian Yang, Dublin, OH (US)

(73) Assignee: The Ohio State University, Columbia, OH (US)

( * ) Notice: Subject to any disclaimer, the term of this patent is extended or adjusted under 35 U.S.C. 154(b) by 0 days.

(21) Appl. No.: 09/422,403

(22) Filed: Oct. 21, 1999

(65) Prior Publication Data

US 2003/0235907 A1 Dec. 25, 2003

Related U.S. Application Data

(62) Division of application No. 08/749,982, filed on Nov. 15, 1996, now Pat. No. 6,033,896.

(51) Int. Cl.⁷ .......................... C12N 11/14; C12N 11/04
(52) U.S. Cl. ...................... 435/176; 435/174; 435/177; 435/182; 435/243; 435/261; 435/283.1; 435/286.1; 435/286.5; 435/289.1; 435/297.1; 435/308.1
(58) Field of Search ................................. 435/174, 176, 435/177, 182, 243, 261, 283.1, 286.1, 286.5, 289.1, 297.1, 308.1

(56) References Cited

U.S. PATENT DOCUMENTS

| | | | |
|---|---|---|---|
| 4,729,958 A | 3/1988 | Drozd et al. ................. | 435/270 |
| 4,791,063 A | 12/1988 | Hou et al. .................... | 435/243 |
| 5,032,508 A | 7/1991 | Naughton et al. ............. | 435/32 |
| 5,563,069 A | 10/1996 | Yang ......................... | 435/295.3 |

OTHER PUBLICATIONS

Absolom, D.R., Thomson C., Kinetics of Cell Adhesion to Polymer Surfaces, pp. 215–229, 1998, *Journal Of Biomedical Materials Research*.

Busscher, H. J.; Sjollema, J.; et al., Relative Importance of Surface Free Energy as a Measure of Hydrophobicity in Bacterial Adhesion to Solid Surfaces, pp. 355–359, 1990, *Microbial Cell Surface Hydrophobicity*.

Cottrell, I.W.; Kang, K.S. et al., Xanthum Gum, Chapter 24, 1980, *Handbook Of Water–Soluble Gums And Resins*.

Daniels, S.L., Mechanisms Involved in Sorption of Microorganisms to Solid Surfaces, pp. 7–58, 1980, *Adsorption Of Microorganisms To Surfaces*.

Discosmo, F.; Tanaka, H. et al., Cell Immobilization by Adsorption to Glass Fiber Mats, pp. 263–287, 1994, *Immobilized Biosystems: Theory and Practical Applications*.

Discosmo, F.; Facchini, P.J. et al., Does the Spontaneous Adhesion of Cultured Plant Cells to Polymer Surface Have Potential as an Immobilization Technique?, pp. 137–140, 1988, *Trends in Biotechnology*.

Gorden, A.S.; Millero, F.J., Electrolyte Effects on Attachment of an Estuarine Bacterium, pp. 495–499, 1984, *Applied And Environmental Microbiology*.

Kang K.S.; Pettitt, D.J., Xanthan, Gellan, Welan, And Rhamsan, pp. 341–371, 1993, *Industrial Gums: Polysaccharides And Their Derivatives*.

Kennedy, J.F.; Bradshaw, I.J., Production Properties and Applications of Xanthan, pp. 319–371, 1984, *Progress In Industrial Microbiology*.

Kirby, A.R., Gunning, A.P., et al., Imaging Xanthan Gum by Atomic Force Microscopy, pp. 161–166, 1995, *Carbohydrate Research*.

Korber, D.R.; Lawrence, J.R. et al, Effect of Motility on Surface Colonization and Reproductive Success of Pseudomans Fluorescens in Dual–Dilution Continuous Culture and Batch Culture Systems, pp. 1421–1429, 1994, *Applied And Environmental Microbiology*.

Lebrun, L., Junter, G.A. et al., Exopolysaccharide Production by Free and Immobilized Microbial Cultures, pp. 1048–1054, 1994, *Enzyme and Microbial Technology*.

Lewis, V.P., Yang S.T.; Continuous Propionic Acid Fermentation by Immobilized Propionibacterium Acidipropionici in a Novel Packed–Bed Bioreactor, pp. 465–474, 1992, *Biotechnology and Bioengineering*.

Margaritis, A.; Pace, G.W., Microbial Polysaccharides, pp. 1005–1043, 1985, *Comprehensive Biotechnology: The Principles, Applications, And Regulations Of Biotechnology In Industry, Agriculture, And Medicine*.

Pace, G.W., Righelato, R.C., Production of Extracellular Microbial Polysaccharides, pp. 41–70, 1980, *Advances n Biochemical Engineering*.

Robinson, D.K.; Wang, D.I.C., A Transport Controlled Bioreactor For The Simultaneous Production And Concentration Of Xanthan Gum, pp. 231–241, 1988, *Biotechnology Progress*.

Rosenberg, M.; Kjelleberg, S., Hydrophobic Interactions: Roles In Bacterial Adhesion, pp. 353–393, 1985, *Advances In Microbial Ecology*.

(List continued on next page.)

*Primary Examiner*—Rodney P Swartz
(74) *Attorney, Agent, or Firm*—Standley Law Group LLP

(57) ABSTRACT

The present invention includes a process for separating cells from a liquid media, a method of fermentation using such a separation, and an apparatus for conducting such a separation or for facilitating a cellular reaction. In broadest terms, the separation process of the present invention is a process for separating cells from a liquid containing cells. The process comprises the steps of: (a) bringing the liquid containing the cells into contact with one or more microbial polysaccharide and a fibrous material so as to adsorb the cells onto the fibrous material; and (b) separating the liquid from the fibrous material so as to remove the cells from the liquid. The process of the present invention may be used to remove cells from any liquid, but such liquids typically will be aqueous solutions, such as growth media, biological fluids, diagnostic samples, aqueous test samples, etc.

16 Claims, 16 Drawing Sheets

OTHER PUBLICATIONS

Shu, C.H., Yang, S.T., Effect Of Temperature On Cell Growth And Xanthan Production In Batch Cultures Of Xanthomonas Campestris, pp. 454–468, 1990, *Biotechnology and Bioengineering*.

Silva, E.M.; Yang, S.T., Kinetics And Stability Of A Fibrous– Bed Bioreactor For Continuous Production Of Lactic Acid From Unsupplemented Acid Whey, pp. 59–70, 1995, *Journal Of Biotechnology*.

Thonart, P.H.; Paquot, M; et al., Xanthan Production By Xanthanomonas Campestris NRRL B–1459 And Interfacial Approach By Zeta Potention Measurement, pp. 235–238, 1985, *Enzyme And Microbial Technology*.

Van Loosdrect, M.C.M., Lyklema, J. et al., Electrophoretic Mobility And Hydrophobicity As A Measure To Predict The Initial Steps Of Bacterial Adhesion, pp. 1898–1901, 1987, *Applied And Environmental Microbiology*.

Yang, S. T.; Zhu, H. et al, Continuous Propionate Production From Whey Permeate Using A Novel Fibrous Bed Bioreactor, pp. 1124–1130, 1994, *Biotechnology And Bioengineering*.

Yang, et al., Xanthan Gum Fermentation by *Xanthomonas campestris* Immobilized in a Novel Centrifugal Fibrous– Bed Bioreactor, pp. 630–637, 1996, *Biotechnol. Prog.* Yang et al., Production of Cell–Free Xanthan Fermentation Broth by Cell Adsorption on Fibers, pp. 259–264, 1998, *Biotechnol. Prog.*

Lo et al., Kinetic and Feasibility Studies of Ultrafiltration of Viscous Xanthan Gum Fermentation Broth, pp. 237–249, 1996, J. Membrane Sci. (117).

Lo, Yang–Ming; A Novel Immobilized Cell Bioreactor and Membrane Ultrafiltration for Xanthan Gum Production, 1995, The Ohio State University.

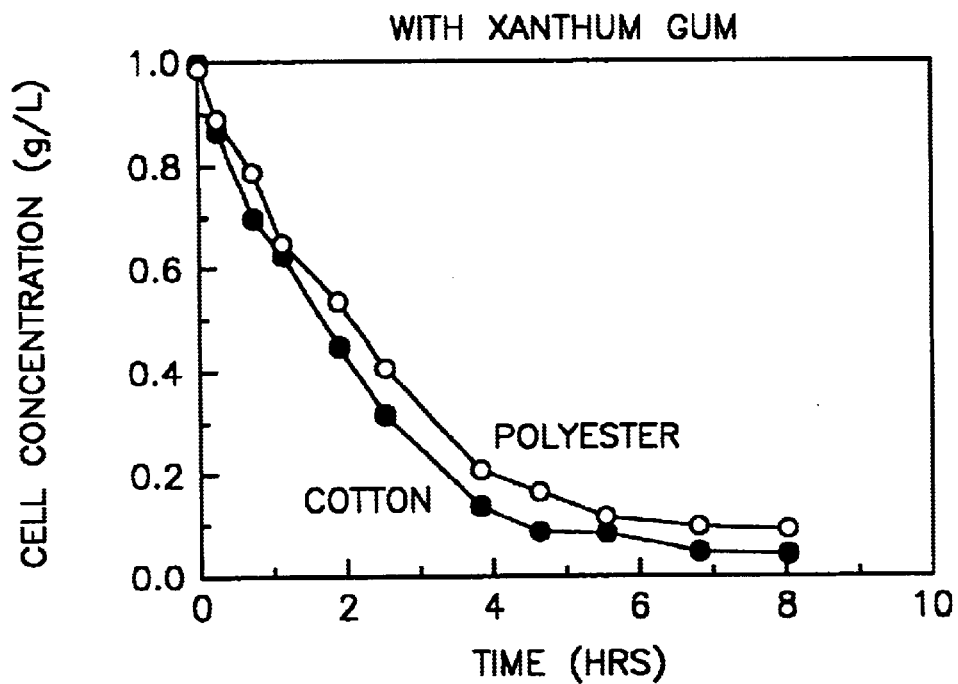
FIG-4(a)
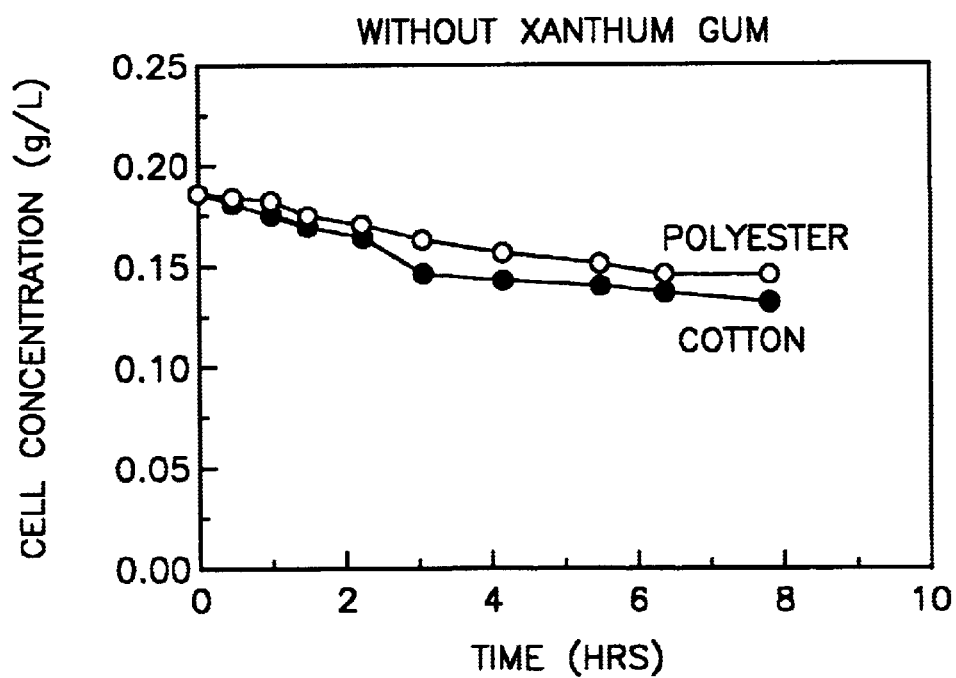
FIG-4(b)
FIG-4

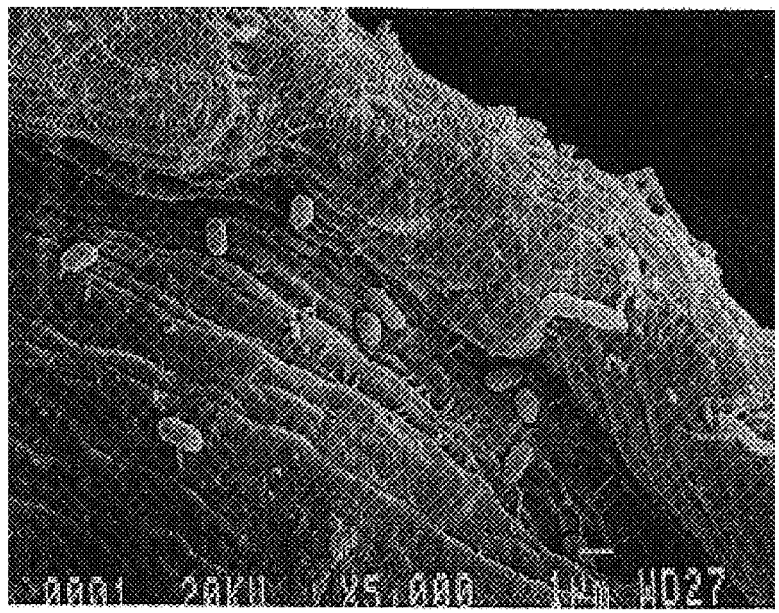
FIG-6(a)
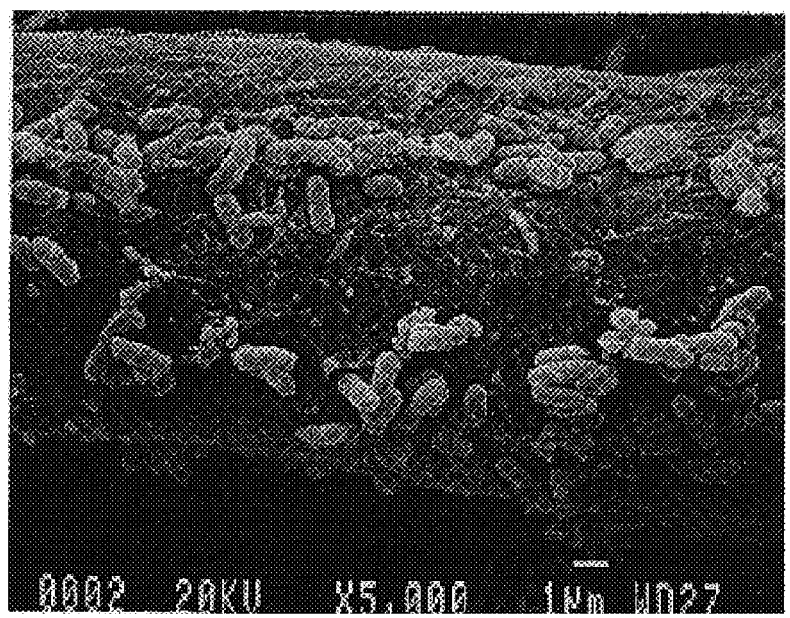
FIG-6(b)
FIG-6

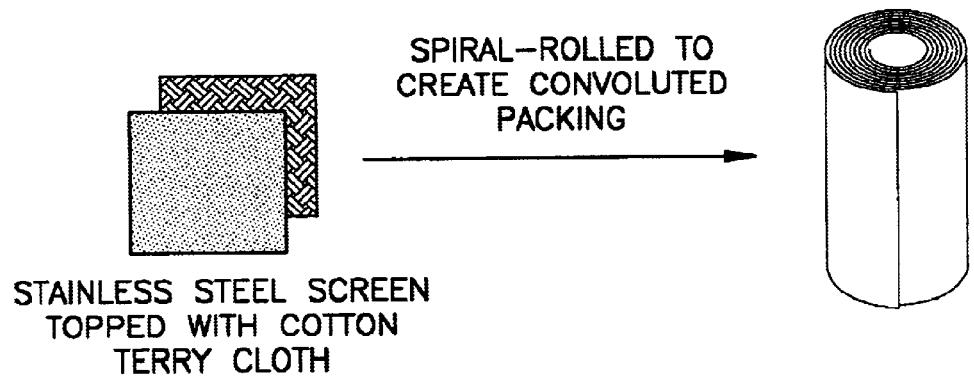
FIG-7(a)
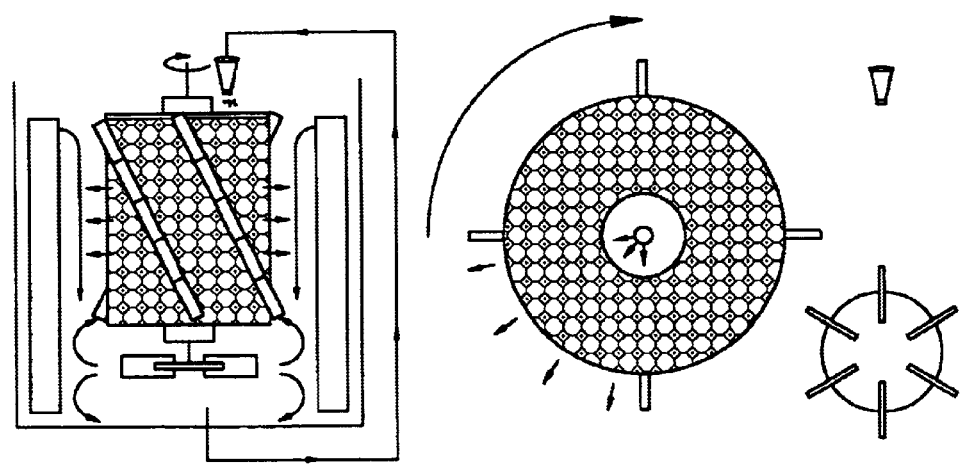
FIG-7(b)
FIG-7

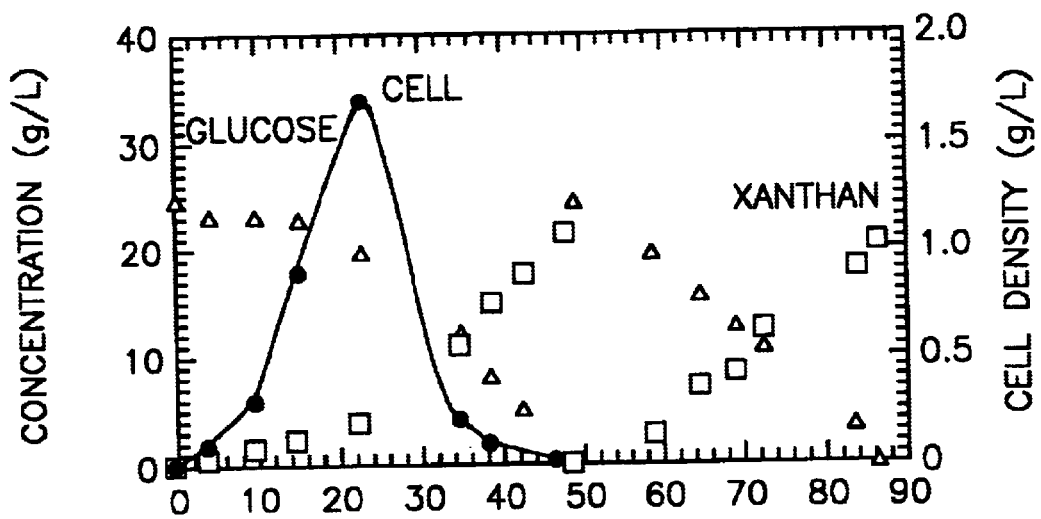
FIG-8(a)
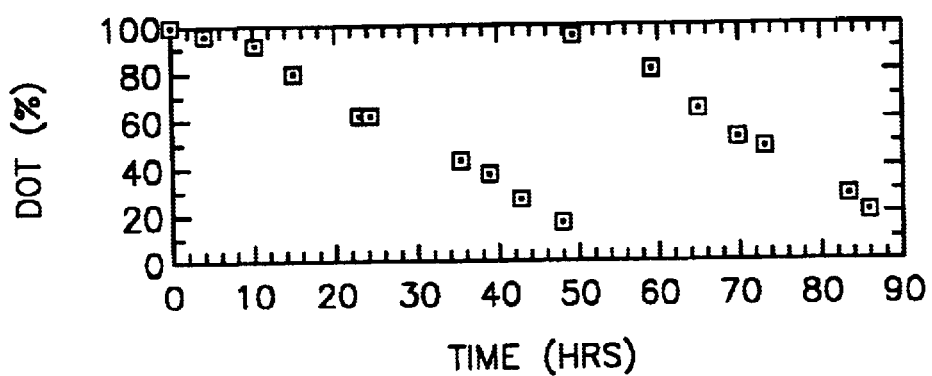
FIG-8(b)
FIG-8

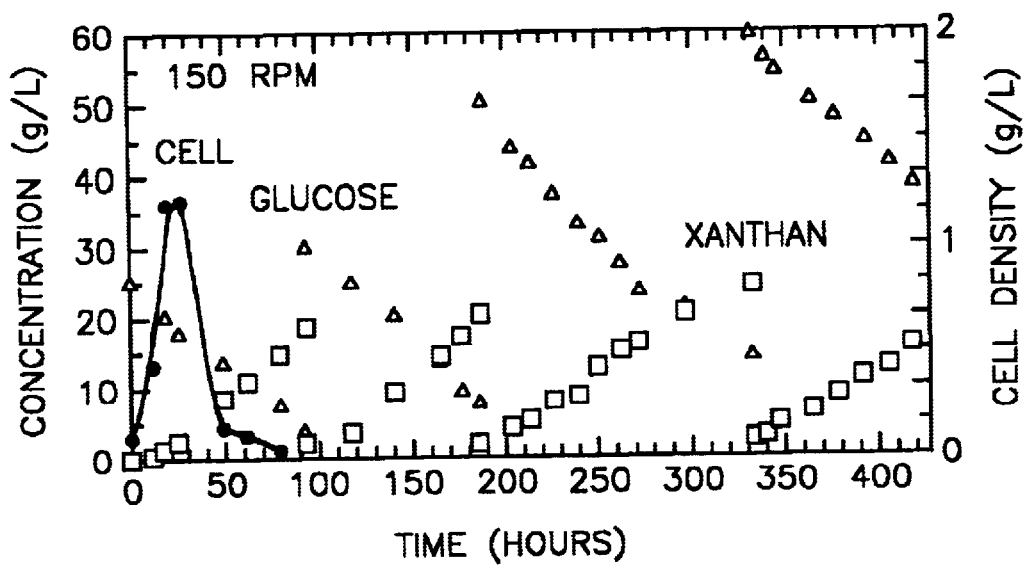
FIG-9(a)
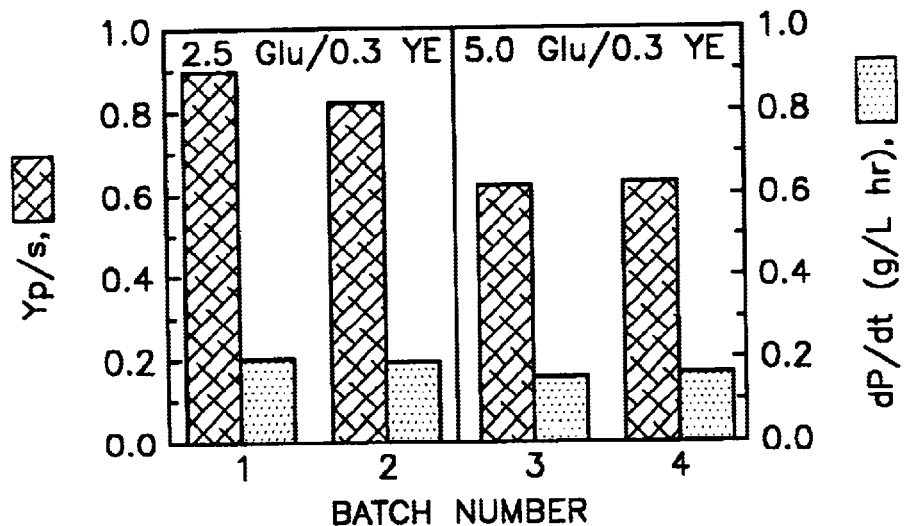
FIG-9(b)
FIG-9

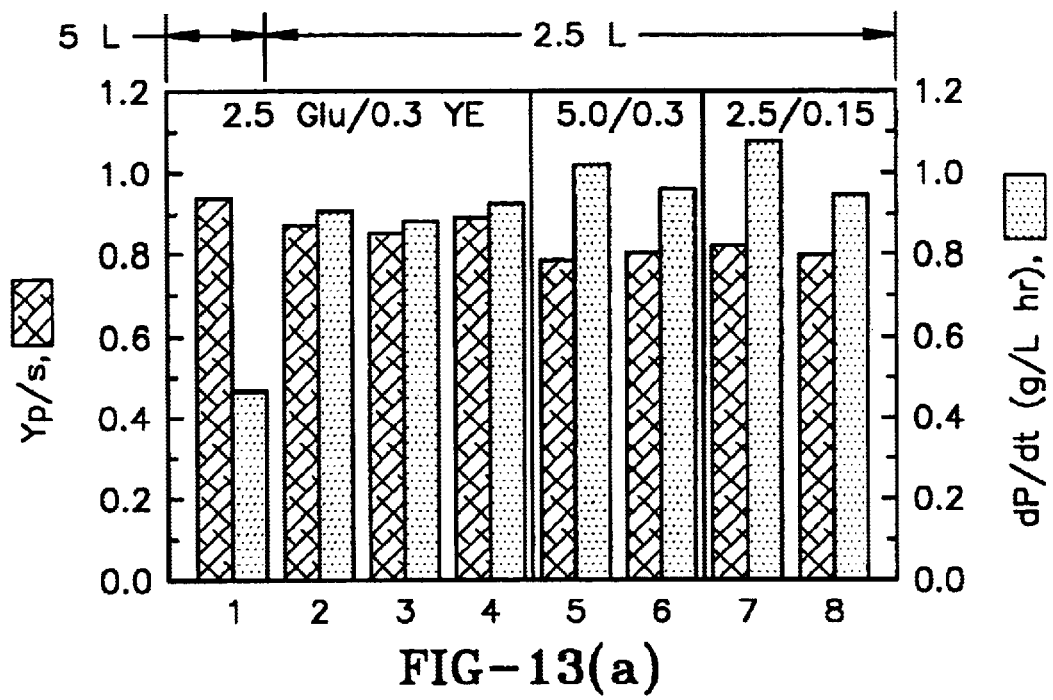
FIG-13(a)
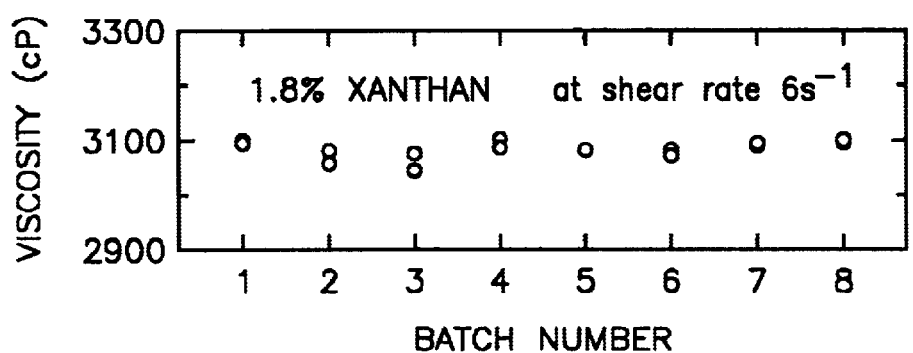
FIG-13(B)
FIG-13

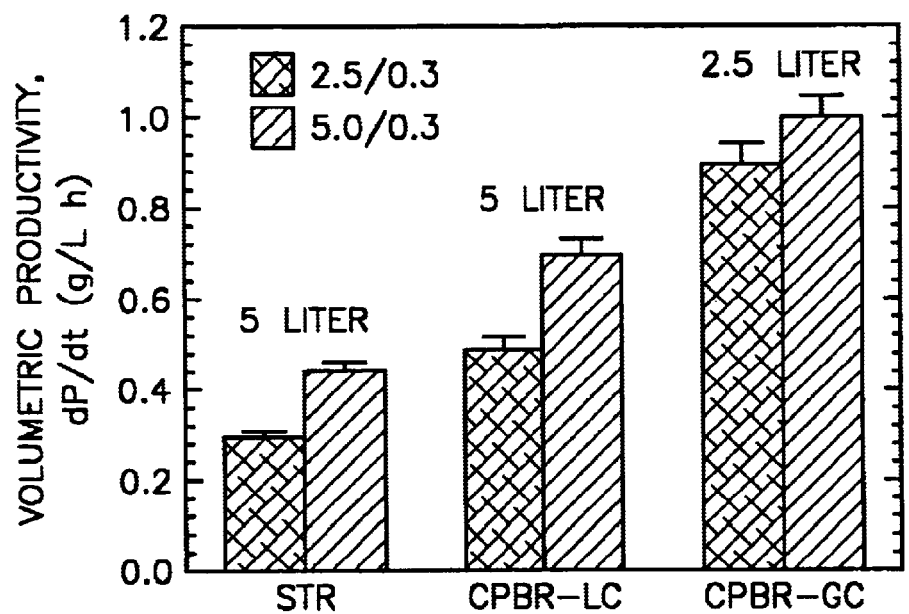
FIG-15(a)
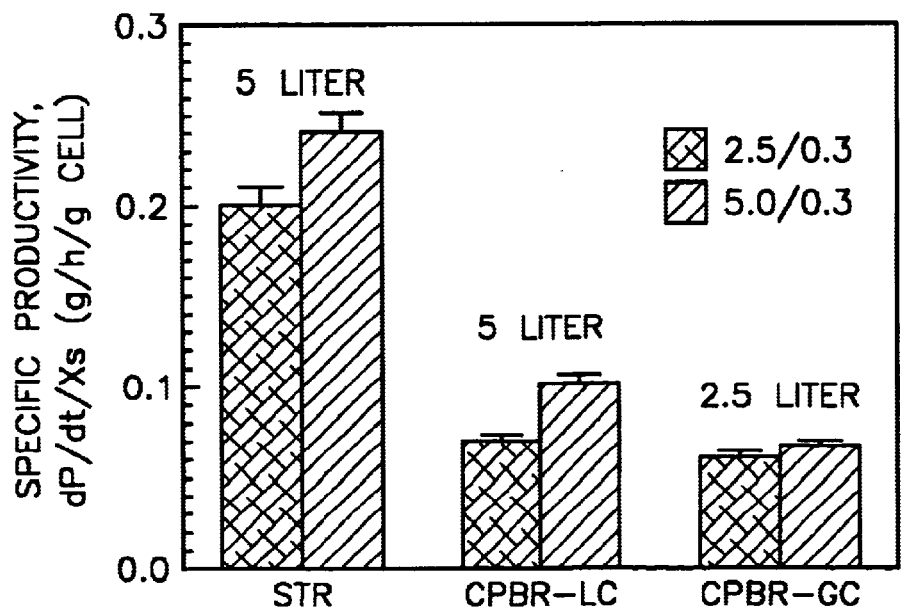
FIG-15(b)
FIG-15

APPARATUS FOR SEPARATING CELLS AND PRODUCING MICROBIAL POLYSACCHARIDES

RELATED APPLICATIONS

This application is a divisional application of U.S. application Ser. No. 08/749,982 filed Nov. 15, 1996 Entitled PROCESS OF SEPARATION OF CELLS FROM LIQUID BY ADSORPTION ONTO FIBER MEDIATED BY MICROBIAL POLYSACCHARIDES, METHOD AND APPARATUS OF PRODUCING MICROBIAL POLYSACCHARIDES USING CELLS IMMOBILIZED ON FIBERS, now U.S. Pat. No. 6,003,896.

TECHNICAL FIELD

The present invention is in the field of biological separations and processes.

BACKGROUND

In a variety of liquids containing cellular material, such as those used in fermentation processes, it is often desirable to be able to efficiently separate cellular products, such as cell bodies, lysed cells, and their breakdown products. It is often desirable to be able to remove or separate cellular products even in instances involving viscous liquids.

Accordingly, it is a general object of the present invention to be able to have available, a process for efficiently and completely removing or separating cellular products from liquid media, even in instances involving viscous liquids.

The process of the present invention can be applied inter alia to fermentation processes. Current industrial fermentations in conventional stirred tank fermentors for production of xanthan gum and other polysaccharides are energy-intensive and costly, mainly because the high broth viscosity causes agitation and aeration to be difficult and limits the final product concentration and productivity.

The production of xanthan gum is described here as an example of some of the problems encountered in biological processes that are addressed by the present invention, although the invention is not limited to that application.

Xanthan gum is a microbial polysaccharide widely used as a suspending, stabilizing, or thickening agent in the food industry. It is also used as a lubricant, emulsifier, or mobility-control agent in the oil-drilling industry. Presently, commercial xanthan gum is produced from glucose or dextrose by batch fermentation with the bacterium *Xanthomonas campestris*; the produced xanthan gum is then recovered and partially purified using alcohol precipitation. The final product usually also contains some cells and cell debris; however, it is desirable to produce xanthan gum product that is free of any particulates or cells, particularly for applications in oil recovery. The production of cell-free xanthan broth also allows for efficient concentration of xanthan fermentation broth by ultrafiltration without significant membrane fouling caused by cells and their debris (e.g., DNA and RNA) that would otherwise be present in the xanthan broth.

The present industrial process for xanthan gum production is energy-intensive and costly, mainly because the highly viscous xanthan broth causes agitation and aeration to be difficult in conventional stirred tank fermentors. Consequently, conventional xanthan gum fermentation has low xanthan concentration (usually below 3% wt/v) and low productivity (usually below 0.5 g/L×h). There have been many attempts to increase xanthan productivity and to lower energy costs by using new agitation designs, and new types of bioreactors. Fermentation with water-in-oil emulsion and cell immobilization using porous Celite beads, which reduces broth viscosity and improves aeration and oxygen transfer, have also been studied. Although a high xanthan concentration of ~5% was achieved in these processes, separating and recovering xanthan gum from the oil emulsion or Celite particles, though feasible, was difficult.

There have been only a few studies of xanthan fermentation using immobilized cells. Robinson and Wang (1988) used porous Celite beads to immobilize cells in xanthan fermentation. It is not clear, however, if the xanthan broth so produced was free of cells. Furthermore, a large portion of the xanthan product was trapped in the beads and could not be easily separated from the cells. Lebrun et al. (1994) studied polysaccharide production by cells immobilized in composite agar layer/microporous membrane structures, but concluded that the immobilized-cell system was not appropriate for xanthan gum production. It is clear that cell entrapment is not an appropriate cell immobilization method for xanthan gum fermentation because of the high viscosity of xanthan solution. The viscosity of the xanthan solution is high even at a low concentration. In batch xanthan fermentation, the broth viscosity has been found to reach more than 3000 cp at 2% (wt/v) xanthan concentration. The high viscosity of xanthan broth presents a major challenge in separating cells and cell debris from broth at industrial scale using conventional separation techniques, such as microfiltration, flocculation, and centrifugation. Thus, one of the objects of the present invention is to find an economical way to produce cell-free xanthan broth by either cell immobilization during fermentation or cell removal after fermentation.

One of the objects of the present invention is to provide a fermentation method which allows for the efficient and substantially complete removal of cells and cell debris from fermentation broths, even in instances involving viscous fermentation broths.

It is also an object of the present invention to allow for the removal of cellular products from liquids used as media for cellular reactions, such as fermentation broths, even those that are unusually viscous.

It is also an object of the present invention to produce an apparatus for carrying out the separation/removal process and cellular reactions of the present invention.

In view of the present disclosure, other advantages and the solutions to related problems may become apparent to one of ordinary skill in the art.

SUMMARY OF THE INVENTION

The present invention includes a process for separating cells form a liquid media, a method of fermentation using such a separation, and an apparatus for conducting such a separation or for facilitating a cellular reaction.

In broadest terms, the separation process of the present invention is a process for separating cells from a liquid containing cells. The process comprises the steps of: (a) bringing the liquid containing the cells into contact with one or more microbial polysaccharide and a fibrous material so as to adsorb the cells onto the fibrous material; and (b) separating the liquid from the fibrous material so as to remove the cells from the liquid. This may be done either by having the microbial polysaccharide(s) be in the liquid or by having the fibrous material be pre-treated with the microbial polysaccharide(s). Either way, a polysaccharide-mediated adsorption of the cells onto the fibrous material is brought about.

The process of the present invention may be used to remove cells from any liquid, but such liquids typically will be aqueous solutions, such as growth media, biological fluids, diagnostic samples, aqueous test samples, etc.

As referred to with respect to the present invention, the term "cells" shall be understood to include, without limitation, cells—alive, dead or attenuated—and cell portions such as lysed cell walls, cell bodies, organelles, chromosome material and mixtures thereof.

The microbial polysaccharide(s) may be of any type. Naturally, there are a wide variety of microbial polysaccharides, such as the more well characterized and named polysaccharides selected from the group consisting of xanthan gum, dextran, pullulan, the polysaccharide types they represent and mixtures thereof.

The liquid may be brought into contact with the microbial polysaccharide and a fibrous material through any appropriate means, such as through the use of tanks and vats, liquid flows, etc.

The fibrous material used in accordance with the present invention may be any natural or synthetic fiber, and may for instance be selected from the group consisting of looped cotton terry cloth, cotton fabric sheet cloth, 50% cotton-50% polyester fabric sheet cloth, and polyester fabric sheet cloth. It has been found that cotton, particularly looped cotton terry cloth and cotton fabric sheet cloth, works best, with looped cotton terry cloth being most preferred.

The fibrous material may be in any non-woven, woven or geometrical arrangement (e.g., sheets, rolls, strands, threads, etc.), generally referred to as the "fibrous matrix," and naturally may be produced and arranged so as to afford efficient contact with the liquid.

The liquid may be brought into contact with the microbial polysaccharide(s) and the fibrous material through any arrangement. Such arrangements may include the use of a liquid container into which a matrix of the fibrous material is placed. As an alternative, the liquid may be brought into contact with the fibrous material by causing the liquid to flow through, within or over a fibrous matrix of the fibrous material. Either the liquid may be moved relative to the fibrous matrix, or vice versa, such as through a liquid flowing over or through the matrix or by having the fibrous matrix mounted on frames and swung or agitated within a container or within a flow of a liquid, etc. The liquid container may also be moved with respect to the liquid, such as through agitation or oscillation. In a preferred embodiment, especially for viscous liquids, the liquid may be brought into contact with the fibrous material by pumping or otherwise forcing the liquid through a fibrous matrix of the fibrous material. This may be done by passing the liquid through a rotating fibrous matrix of the fibrous material through application of centrifugal force, such as by placing the liquid in the interior of the fibrous matrix and spinning it so as to move the liquid from its interior to its outer surface, through application of centrifugal force.

The ultimate separation of the cells from the remaining liquid also may be done through any appropriate means, such as through draining the liquid from the fibrous matrix, the physical removal of the fibrous matrix from the liquid, etc., as each application may require.

The separation process of the present invention, as summarized above, may be used as part of a method for producing a product liquid containing one or more reaction product(s) of a cellular reaction, which liquid is substantially free of cells. In general terms, the method includes the steps: (a) preparing a reaction mixture of: (i) water; (ii) one or more substrate substance(s) for the cellular reaction; (iii) cells of an organism capable of converting the substrate substance(s) to one or more reaction product(s); and (iv) one or more microbial polysaccharide(s); and (b) allowing the reaction mixture to undergo the cellular reaction so as to form the at least one reaction product from the at least one substrate substance; followed by (c) bringing the reaction mixture into contact with a fibrous material so as to adsorb the cells onto the fibrous material, and (d) separating said fibrous material from the reaction mixture so as to remove the said cells from the reaction mixture.

As referred to with respect to the production methods of the present invention, it will be understood that "cellular reaction" is intended in its broadest sense and may be any chemical reaction and/or physical change brought about by or catalyzed by cells of an organism. Such cells may be those of one-celled organisms or the cells of multi-celled organisms, whether microbial plant or animal. Such cellular reaction may be those carried out for industrial production purposes, or for pure or applied research. Typically, cellular reactions in which the present invention may be applied will include those that rely upon enzymatic reactions, both anabolic and catabolic.

The cellular reactions may involve one or more substrate substances which are broadly intended to mean any one or more substances that are the subject of the cellular reaction. In turn, the cellular reaction may produce one or more reaction products. Such product(s) may be obtained through the use of reaction conditions appropriate to the cellular reaction of interest.

Once the reaction product(s) is/are formed, the reaction mixture is brought into contact with a fibrous material so as to adsorb the cells onto the fibrous material. The fibrous material may then be separated from the reaction mixture so as to remove the cells from the reaction mixture.

In a variation of the basic cellular reaction process, it may be the case that the substrate substance(s) and/or reaction product(s) comprise(s) one or more microbial polysaccharide(s) and thus supplies the microbial polysaccharide(s) required in the method of the present invention in the form of a substrate or reaction product. In such cases, the microbial polysaccharides(s) need not be added.

In another variation, the microbial polysaccharides may be applied to the fibrous material, rather than being put into the liquid or arising from the cellular reaction.

The present invention also includes a method for producing xanthan gum solution substantially free of cells using the separation process of the present invention as summarized above. The method generally comprises the steps: (a) preparing a fermentation broth mixture of: (i) water; (ii) a saccharide selected from the group consisting of glucose, dextrose and mixtures thereof; and (iii) *Xanthomonas campestris* bacterial cells; (b) allowing the fermentation broth mixture to undergo fermentation so as to form xanthan gum polysaccharide in the fermentation broth mixture; followed by (c) bringing the fermentation broth mixture into contact with a fibrous material so as to adsorb the bacterial cells onto the fibrous material, and (d) separating the fibrous material from the fermentation broth mixture so as to remove the cells from the fermentation broth mixture (herein "separating" is intended broadly, whether removing the fibrous material from the broth or allowing the broth to flow from the fibrous material).

The invention also includes an apparatus that may be used for carrying out the separation process of the present invention, and which also may be used in accordance with the production methods using the separation process. The apparatus in broad terms is one for separating cells from a liquid containing the cells and comprises: (a) a matrix of a fibrous material treated with one or more microbial polysaccharide(s) having an interior and an outer surface; (b) liquid application dispenser for dispensing the liquid into the interior of the matrix of the fibrous material; and (c) an apparatus to separate the liquid form the matrix of fibrous material. For example, a spinner may be adapted to spin the matrix of a fibrous material such that the liquid, once in the interior of the matrix of the fibrous material, moves out of the outer surface of the matrix of the fibrous material. The fibrous material may become treated with one or more microbial polysaccharide(s) through microbial polysaccharide(s) being resident in the liquid either naturally occurring or arising as a result of a cellular reaction. In an alternative embodiment to those described, where the fibrous material is not pretreated with microbial polysaccharide(s), the apparatus may contain a liquid to be supplied to the liquid application dispenser, the liquid containing at least one microbial polysaccharide and cells of an organism capable of converting the substrate substance(s) to the reaction product(s), such that when the liquid is brought into contact with the matrix of said fibrous material, said cells become adsorbed onto said fibrous material.

The apparatus may additionally include a recirculator adapted to recirculate liquid moving out of the outer surface of the mass of the fibrous material into the interior of the mass of the fibrous material, in order to increase the exposure of the polysaccharide-treated fibrous material to the cells over time. Such a device may be in the form of a recirculating pump or other appropriate flow control device.

The invention also includes an apparatus for facilitating a method for producing a cellular reaction product in a liquid, the apparatus comprising: (a) a matrix of a fibrous material having an interior and an outer surface, the fibrous material treated with at least one microbial polysaccharide and having adsorbed thereupon cells of an organism capable of converting the at least one substrate substance to the at least one reaction product; and (b) a liquid circulator device for circulating the liquid through the matrix of the fibrous material.

The invention also includes an apparatus for facilitating a method for producing a cellular reaction product in a liquid, the apparatus comprising: (a) a matrix of a fibrous material having an interior and an outer surface, the fibrous material treated with at least one microbial polysaccharide and having adsorbed thereupon cells of an organism capable of converting the at least one substrate substance to the at least one reaction product; (b) a reaction vessel for holding the liquid; (c) a liquid transport device adapted to move the matrix of the fibrous material relative to the liquid, such as through agitation or oscillation, for example.

The present invention also includes an apparatus for facilitating a method for producing a cellular reaction product in a liquid. The apparatus comprises a matrix of a fibrous material having an interior and an outer surface, the fibrous material treated with at least one microbial polysaccharide and having adsorbed onto it cells of an organism capable of converting one or more substrate substance to one or more reaction product. The apparatus also includes a liquid application dispenser for dispensing the liquid into the interior of the matrix of the fibrous material; and a spinner adapted to spin the matrix of a fibrous material such that the liquid, once in the interior of the matrix of the fibrous material, moves through the matrix of a fibrous material toward the outer surface of the matrix of the fibrous material so as to bring the liquid in contact with the cells of the organism.

In an alternative embodiment to those described above, the fibrous material is not pretreated with microbial polysaccharide(s), and in such case the apparatus may contain a liquid to be supplied to the liquid application dispenser, the liquid containing at least one microbial polysaccharide and cells of an organism capable of converting the substrate substance(s) to the reaction product(s), such that when the liquid is brought into contact with the matrix of the fibrous material, the cells become adsorbed onto the fibrous material.

The apparatus of the present invention in all its embodiments may include fluid containment and/or conduction apparatus to allow the operator to cause (1) the liquid to flow through a fibrous matrix of the fibrous material, (2) pump the liquid through a matrix of the fibrous material, (3) agitate the liquid in a vessel containing a matrix of the fibrous material; (4) pass a matrix of the fibrous material through the liquid, (5) agitate a matrix of the fibrous material within the liquid and/or (6) force the liquid through a rotating matrix of the fibrous material through application of centrifugal force. Such apparatus may be supplied using liquid containment and/or conduction devices known in the art and which could be applied to bring about the desired result in accordance with the parameters of the specific separation or reaction to which the apparatus is to be applied. Examples may include arrangements of reaction vats, pumps and liquid conduits to contain the liquid and bring it into contact with the fibrous matrix.

The apparatus may additionally include a recirculator adapted to recirculate liquid within the fibrous matrix, such as by moving out of the outer surface of the mass of the fibrous material into the interior of the mass of the fibrous material so as to increase the exposure of substrate to the adsorbed cells over time.

In applications involving viscous liquids, it is preferred that the fibrous matrix be exposed to air and spun at such a rate that such that the viscosity is overcome by the mechanical shearing.

The high viscosity of a xanthan solution at low concentration presents a major challenge in agitating xanthan broth during fermentation. Xanthan solution, however, shows a high degree of pseudoplasticity, i.e., the viscosity decreases rapidly as the shear rate increases. This shear-thinning property allows efficient pumping of xanthan polymer at high pumping (shear) rates. The present invention thus includes a centrifugal, fibrous-bed bioreactor that may be used for instance for viscous xanthan gum fermentation, and in other processes that present similar problems of viscosity and the need for contact with cells. Difficulties in agitation and aeration in the conventional stirred-tank bioreactors, such as those used in traditional fermentation, are overcome by continuous medium recirculation through a rotating fibrous matrix, which contained immobilized cells. In this bioreactor, liquid media and air (or other oxygen-containing gas) were passed through the porous fibrous matrix to ensure intimate contact with the immobilized cells, thus achieving high oxygen transfer and reaction rates. The centrifugal force generated from rotating the fibrous matrix separated the xanthan polymer from the immobilized cells, thus producing a cell-free xanthan broth. It is important to produce xanthan gum solution free of any particulates or cells for applications in oil recovery. The production of cell-free xanthan broth also allows one to efficiently concentrate the xanthan fermentation broth by ultrafiltration without significant membrane fouling caused by cells and resulting debris (e.g., DNA and RNA) that would otherwise be present in the xanthan broth.

BRIEF DESCRIPTION OF THE DRAWINGS

FIG. 4 shows two graphs of cell concentration vs. time showing the kinetics of cell adsorption to fibrous bed; graph (a) in the presence of xanthan gum, and graph (b) in the absence of xanthan gum.

FIGS. 6(a) and (b) shows two scanning electron micrographs showing adsorption of *Xanthomonas campestris* cells and xanthan gum on a cotton fiber surface.

FIG. 7 shows a schematic diagram of the centrifugal, packed-bed reactor (CPBR) showing (a) construction of fibrous matrix, and (b) fluid flow pattern in the reactor, that may be used for a process such as xanthan gum fermentation, in accordance with one embodiment of the present invention.

FIG. 8 shows two graphs pertaining to typical kinetics during reactor start-up: (a) a plot of concentration vs. cell density and (b) a plot of DOT vs. time.

FIG. 9 shows two graphs pertaining to repeated batch xanthan fermentations with CPBR at 150 rpm rotational speed for the fibrous bed: (a) a plot of concentration vs. time and (b) a bar graph of xanthan yield (Yp/s) and volumetric xanthan productivity (dP/dt) for four batches.

FIG. 13 shows two graphs pertaining to batch xanthan fermentations with CPBR-GC at 350 rpm rotational speed for the fibrous bed: (a) a bar graph of xanthan yield (Yp/s) and volumetric xanthan productivity (dP/dt) for eight batches, and (b) a plot of measured broth viscosity at 1.8% xanthan concentration, in accordance with one embodiment of the present invention.

FIG. 15 shows two graphs pertaining to a comparison of reactor performance and effect of C/N ratio: (a) a plot of volumetric productivity (dP/dt) for stirred tank reactor (STR), CPBR-LC and CPBR-GC, and (b) a plot of specific productivity (dP/dt/Xs) for STR, CPBR-LC, and CPBR-GC with two different glucose concentrations (2.5% and 5%) and the same 0.3% yeast extract concentration in the media.

DETAILED DESCRIPTION OF THE PREFERRED EMBODIMENTS

In accordance with the foregoing summary, the following presents a detailed description of the preferred embodiment of the present inventions as they might be applied to the fermentation of xanthan gum.

EXAMPLE 1

The Production of Cell-Free Xanthan Fermentation Broth by Cell Adsorption on Fibers The following Example shows the use of a method of removing cells from a liquid cellular reaction media (i.e., a fermentation broth) in accordance with one embodiment of the present invention.

Materials and Methods

Culture and Medium

*Xanthomonas campestris* NRRL B-1459, originally obtained from the Northern Regional Research Laboratory (NRRL) of the U.S. Department of Agriculture (Peoria, Ill.), was used. Stock cultures of *X. campestris* NRRL B-1459 were maintained on agar slants, which contained 10 g/L glucose, 3 g/L yeast extract, 5 g/L peptone, and 15 g/L agar, and were stored at 4° C. The culture was transferred once every two weeks to maintain good viability and stability for xanthan production. The medium used in fermentation consisted of 25 g/L glucose, 3 g/L yeast extract, 2 g/L $K_2HPO_4$, and 0.1 g/L $MgSO_4 \times 7H_2O$. Tap water was used in preparing the medium to provide trace elements. The medium pH was adjusted to 7 by adding 4N HCl.

Cell Adsorption to Fibers during Fermentation

Four different woven fibrous materials were used for cell adsorption during batch fermentation, including cotton towel (terry cloth, ~5 mm thick), cotton fabric sheet (without looping, ~1 mm thick), 50% cotton-50% polyester fabric sheet (~1 mm thick), and polyester fabric sheet (~1 mm thick). Each fibrous sample was tested for its cell adsorption capability by placing a small piece (3 cm×3 cm) of the fibrous material in a 500-mL fermentation flask containing 100 mL media. The flask was sterilized, inoculated with *X. campestris*, and then incubated in an incubator-shaker at 30° C. and 300 rpm shaking speed. The suspended cell density in each flask was monitored by measuring the optical density of the broth at regular time intervals for 50 hours. The attachment of *X. campestris* cells on each fibrous matrix was examined at the end of the experiment by using scanning electron microscopy (SEM).

Batch fermentation was then carried out in a 5-L fermentor containing a packed bed of cotton towel mounted on the reactor impeller shaft. The bioreactor was autoclaved, filled with 5 liter of sterile media, and then inoculated with 100 mL flask culture. Unless otherwise noted, the cells in the bioreactor were first grown at pH 6 and 23° C., the optimal conditions for cell growth. The bioreactor was aerated at a volumetric flow rate of 5.0 std. liter/min. and agitated at 150 rpm. After ~24 hours, the reactor conditions were changed to pH 7, 30° C., and 350 rpm to promote xanthan production. Samples were taken for analyses of glucose concentration, cell density, and xanthan concentration.

Cell Adsorption to Fibers after Fermentation

Figure 1:
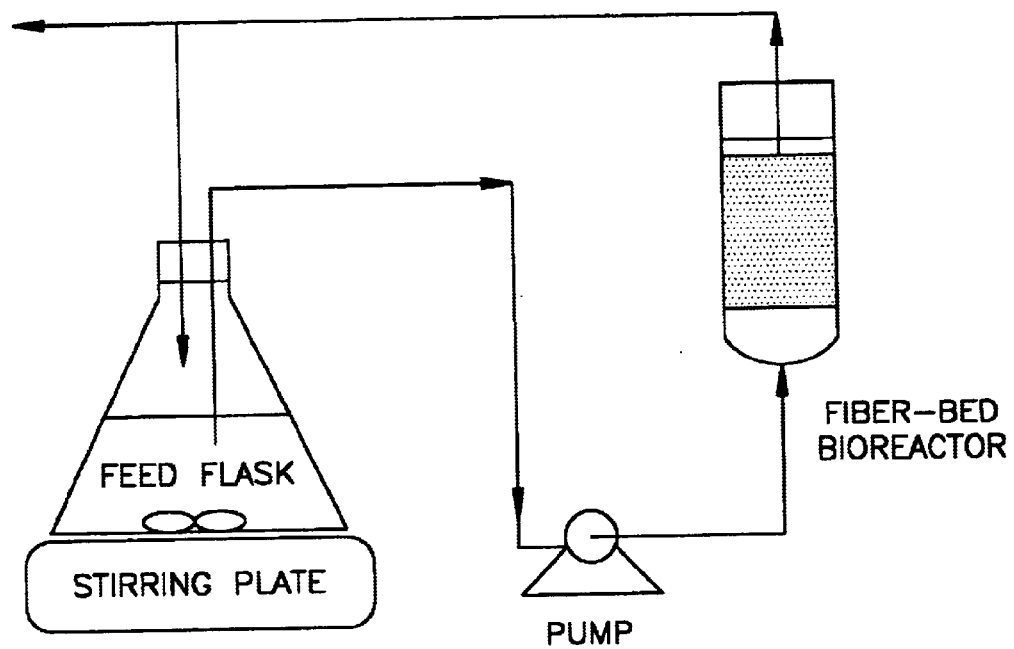
FIG. 1 is a schematic diagram of the packed fibrous-bed for study of cell adsorption kinetics in accordance with one embodiment of the present invention.

The kinetics of cell adsorption to fibers was further studied using cell suspension harvested from flask cultures. FIG. 1 shows the schematic diagram of the experimental apparatus used in studying cell adsorption. The cell suspension was circulated through a fibrous bed packed in a glass column (dimensions: 2.7 cm diameter.×9 cm height) with a total liquid volume of ~42 mL. The fibrous materials were pre-wetted with distilled water, and the complete system was autoclaved for 30 minutes before use. A peristaltic pump (such as sold under the name Masterflex by Cole Parmer of Chicago, Ill.) was used to pump the cell suspension (~300 mL) from the flask through the fibrous bed at a flow rate of 5.9 mL/min. to approximate well-mixed condition in the flask. Samples were taken from the flask at regular time intervals to monitor the cell concentration change with time. These data were then used to study the adsorption kinetics and to determine the adsorption rate constant. All experiments were done at the room temperature (~25° C.).

Experiments were conducted with cells with and without their exopolysaccharide, xanthan gum, to determine the effect of xanthan gum on cell adsorption. Cells were first grown in flasks for two to three days. The whole broth containing cells and xanthan gum was then used in the adsorption experiment. Experiments were also conducted with cell suspension in a salt solution without xanthan gum. To prepare xanthan-free cell suspension, the fermentation broth was first diluted with water and centrifuged at 16,000 g for 30 min. to separate the cells from the broth containing xanthan gum. The cells were then collected and re-suspended in a salt solution, and the cell suspension was then used in the adsorption experiments. Two different fibrous materials, cotton and polyester, were studied to evaluate the effect of fiber surface properties on cell adsorption.

Determination of Cell Density

Samples of fermentation broth were collected into centrifuge tubes. Depending on the broth viscosity, the broth samples were diluted with tap water by a factor of two to six, and the diluted solutions were centrifuged at 12,000 rpm (16,000 g) for 30 minutes at 5° C. to precipitate the cells. Cells were then re-suspended in water and the optical density at 650 nm ($OD_{650}$) was measured using a spectrophotometer. The OD readings were then compared to a standard correlation between OD and cell density (g/L). The cell density was proportional to OD when the optical density was below 0.5, with one unit of OD equaling to 0.4 g/L cell. The total cell dry weight in the cell suspension was also determined after drying at 105° C. for ~7 hours in a vacuum oven. The dry weight measurement was duplicated to reduce the experimental errors to within 0.2%.

Scanning Electron Microscopy

Several small pieces of the fibrous material were taken as samples from the drained fibrous matrix. These samples were immersed in 2.5% glutaraldehyde solution overnight and then rinsed completely with double distilled water. The samples were then gradually dehydrated with 20%–100% ethanol in increments of 10% by holding the samples at each concentration for 30 min. These samples were then cryogenically dried at critical point with liquid $CO_2$. All steps, except for the critical drying, were carried out at 4° C. The completely dried samples were coated with gold/palladium before taking SEM photographs using the JOEL model 820 SEM.

Adsorption Kinetics

Adsorption of cells to substrates (fibers) can be considered to be a reversible surface reaction, as follows:

$$C + S \underset{k_d}{\overset{k_a}{\rightleftharpoons}} C - S \qquad 1$$

where C is the cell concentration, S is the concentration of substrate or active site on the substrate surface, C–S is the cell-substrate complex, and $k_a$ and $k_d$ are adsorption and desorption rate constants, respectively. When there is no diffusion limitation, the rate of formation of the cell-substrate complex or the cell adsorption rate can be expressed as follows:

$$-\frac{dC}{dt} = k_a SC - k_d C - S \qquad 2$$

where t is the reaction time. Initially, adsorption of cells on the substrate predominates as C–S is zero or negligibly small. When the adsorption rate is much greater than the desorption rate, the desorption term in equation (2) can be neglected. Also, when S>>C, S can be considered as a constant and S≈$S_0$. Equation (2) is thus reduced to equation (3).

$$-\frac{dC}{dt} \approx k_a SC \approx k_a S_o C \qquad 3$$

Equation (3) can be integrated to the following form:

$$\ln\left(\frac{C}{C_o}\right) = -k_a S_o t \qquad 4$$

where $C_0$ is the initial cell concentration and $S_0$ is the initial substrate concentration.

If cell adsorption does follow the first-order reaction kinetics, a semi-logarithmic plot of $C/C_0$ versus time should yield a line with a slope equal to $-k_a S_0$. The adsorption rate constant, $k_a$, thus can be determined from the slope and $S_0$. Cell adsorption to fiber surface is not specific to "active sites" on the substrate surface. Since the surface area available to cell adsorption is proportional to the amount of the fibers present in the fibrous bed, the packing density (g/L) of the fiber in the fibrous bed was used as $S_0$ in this embodiment of the present invention.

Results

Cell Adsorption to Fiber during Fermentation

Figure 2:
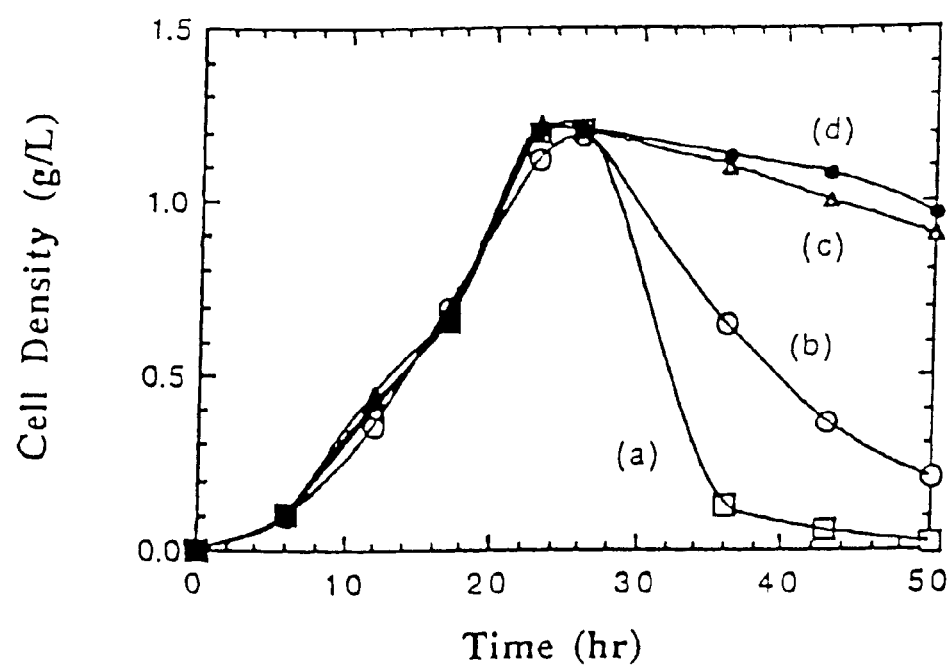
FIG. 2 is a graph of cell density vs. time showing changes of cell concentration during batch xanthan gum fermentation in flasks containing various types of woven fibrous materials:—(a) cotton towel, (b) cotton fabric sheet, (c) 50% cotton/50% polyester fabric sheet, and (d) polyester fabric sheet.

FIG. 2 shows the cell concentration changes during four batch xanthan fermentations with various fibrous materials in the flasks for cell adsorption. While xanthan production was not affected by the types of fibrous materials studied (data not shown), the 100% cotton towel with looping showed the fastest cell adsorption rate and had adsorbed almost all suspended cells by 50 hours fermentation time. The other materials also adsorbed cells, but at slower rates. In general, the hydrophilic cotton fiber was preferable to the hydrophobic polyester fiber, and more cells were attached to the 100% cotton towel than the other materials studied. The rough surface of cotton fibers and the looping of the towel seemed to be important factors for cell adsorption under the condition studied.

Figure 3:
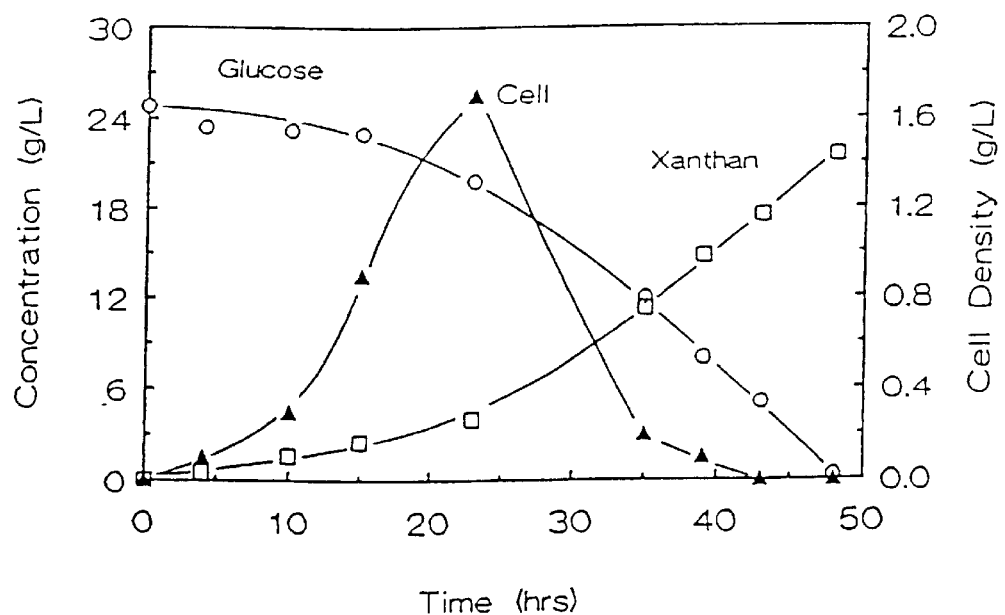
FIG. 3 is a graph of concentration/cell density vs. time showing the kinetics of a typical batch fermentation with cotton towel in the fermentor for cell adsorption (immobilization).
Figure 5:
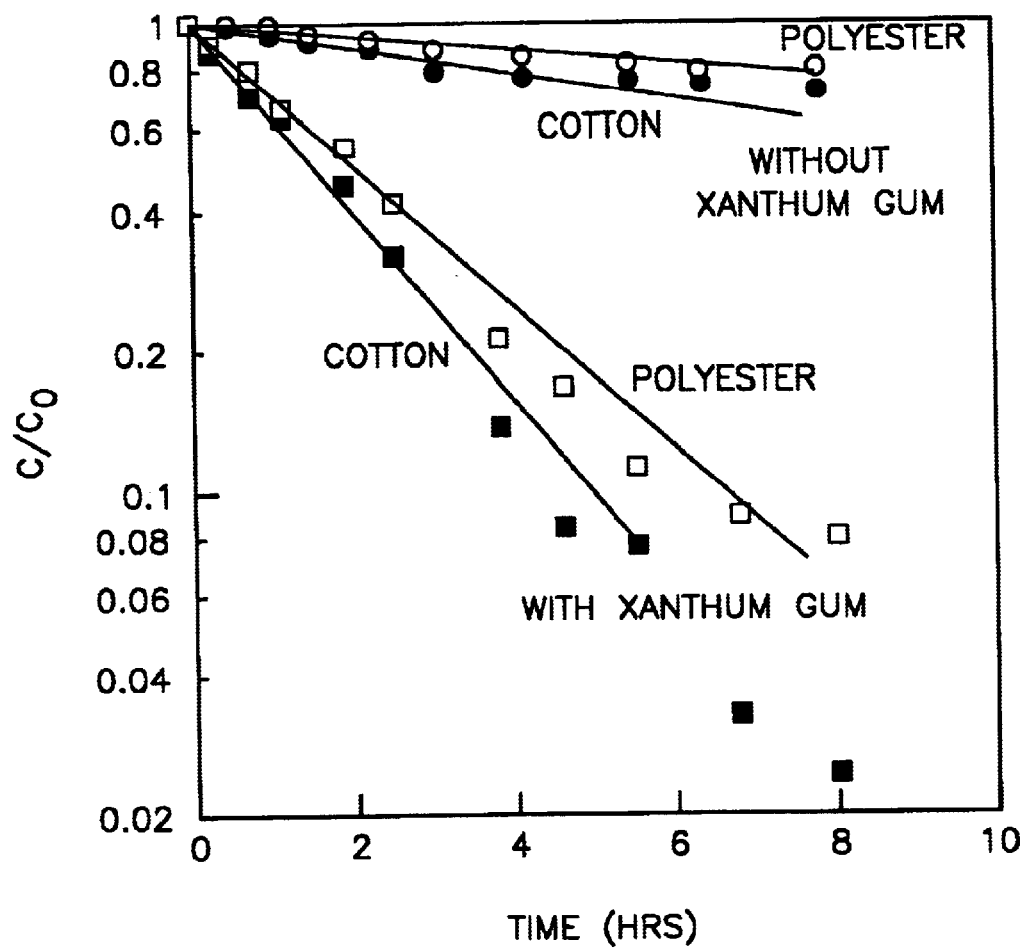
FIG. 5 is a semi-logarithmic plot of $C/C_0$ vs. time, showing the kinetics of cell adsorption to a variety of fibers.

Batch xanthan fermentation was carried out with cotton towel present in the fermentor for cell adsorption. As shown in FIG. 3, exponential cell growth, but only small amounts of xanthan biosynthesis, occurred during the initial 24 hour period, a pattern which is also typical of xanthan gum batch fermentation with free cells. At ~24 hours, when the culture reached the stationary phase, the cell density in the fermentation broth rapidly decreased while xanthan production continued to increase, indicating that the cells were immobilized (adsorbed) onto the matrix. All suspended cells disappeared and were immobilized onto the fibrous matrix by 50 hours, as indicated by the broth optical density of being zero. It appeared that the onset of cell adsorption coincided with the onset of xanthan production in the fermentation, suggesting that the production of xanthan gum helped or triggered cells to attach onto the fiber surfaces. Further discussions of the effect of xanthan gum on cell adsorption is given below.

Cell Adsorption to Fiber after Fermentation

The removal of cells from the fermentation broth by pumping the cell suspension through the fibrous bed was studied. FIG. 4 shows the kinetics of cell adsorption to the fibrous bed. In the presence of xanthan gum, the cell concentration in the broth was reduced from 1 g/L to 0.024 g/L with cotton and to 0.074 g/L with polyester, resulting in an almost cell-free xanthan broth. Complete cell removal was possible if longer time or more fibers were used for cell adsorption. Table 1 shows the amounts of cells adsorbed and cell loadings on each of the two fibrous materials studied. It is clear that large amounts of cells can be efficiently removed from the fermentation broth by adsorption of cells to fiber surfaces. A fibrous bed thus can be used to remove *X. campestris* cells from the xanthan fermentation broth.

TABLE 1

Cell adsorption to cotton and polyester

| Conditions | Amt. of fiber used (g) | Packing Density, $S_o$ (g/mL) | Total Cell Adsorbed (mg) | Cell Loading (mg/g) | $k_aS_o$ ($h^{-1}$) | $k_a$ (mL/g × h) |
|---|---|---|---|---|---|---|
| with xanthan gum | | | | | | |
| Cotton fiber | 2.45 | 0.058 | 290.8 | 118.7 | 0.423 | 7.25 |
| Polyester fiber | 2.40 | 0.057 | 272.9 | 113.7 | 0.328 | 5.74 |
| w/o xanthan gum | | | | | | |
| Cotton fiber | 2.94 | 0.070 | 17.7 | 6.0 | 0.061 | 0.87 |
| Polyester fiber | 2.55 | 0.061 | 13.3 | 5.2 | 0.037 | 0.61 |

Cell adsorption to fibers was slow and ineffective when xanthan gum had been removed from the cell suspension. As can be seen in FIG. 4*b*, under xanthan-free conditions only ~24% and ~30% of the cells initially present in the cell suspension were adsorbed to polyester and cotton fibers, respectively. This clearly indicated that cell adsorption was facilitated by the anionic exopolysaccharide, xanthan gum.

Adsorption Kinetics

As shown in FIG. 5, cell adsorption to fibers, both cotton and polyester, followed the first-order (monolayer) adsorption kinetics, which has also been reported for the adsorption of *Pseudomonas florescens* on glass surfaces. The adsorption rate constants for various experimental conditions were calculated from the slopes of these linear plots and are listed in Table 1.

Discussion

Although not limited to the theory of the invention's operation, the factors responsible for cell adsorption on surfaces can be categorized as specific and non-specific. The fibrous material substrates used in the present invention are non-biological and are essentially inert to the cells. The process of non-specific cell adsorption are known to be affected by: (i) character of microorganism (species, culture age, concentration), (ii) character of adsorbent (surface properties such as hydrophobicity and roughness, ionic form, charge, size), and (iii) environmental factors (culture medium, pH, inorganic salt concentration, presence of organic compounds, liquid flow velocity, contact time, temperature).

Hydrophobic interactions are important to cell adhesion to surfaces. Cell adhesion increases linearly with increasing surface hydrophobicity (or decreasing substrate surface tension) when the surface tension of the suspending liquid is larger than the surface tension of the adhering cells; conversely, adhesion increases with increasing surface hydrophilicity (or increasing substrate surface tension) when bacterial surface tension is larger than that of the suspending liquid. In most cases studied previously, it is the first case that prevails; i.e., cells adsorption to hydrophobic surface is generally better than to hydrophilic surfaces.

In this example of the present invention, only two types of fibers with different surface properties were used. The cotton (cellulose) fiber is more hydrophilic and has rough surfaces, whereas polyester fiber is more hydrophobic and has a smooth surface. As can be seen in FIG. 5 and Table 1, cell adsorption to cotton fibers was faster than to polyester fiber. The adsorption rate constants were 30–40% higher for cotton than for polyester. Thus, the adsorption mechanism cannot be solely explained by the surface hydrophobicity.

The structure of the woven fibrous sheet materials can be considered as filters where chromatographic effects can have a deterministic role in the adsorption mechanism of cells to the fibers. The surface roughness of the cotton fibers thus may be the major factor responsible for enhancing cell adsorption. Rough surfaces may provide more surface area per unit weight of the fiber material than smooth surface can. Also, under the flow conditions studied, the rough surfaces of cotton fibers may induce more turbulence and thus increased the contact frequency of cells with the fiber. It might also prevent adsorbed cells from being sheared off the surface due to fluid motion.

The influence of electrostatic interactions is also important to cell adsorption. It is not known if the two fiber materials used in this embodiment carried any surface charges. Bacterial attachment is generally increased by electrolytes at low ionic strengths. Xanthan gum is an anionic heteropolysaccharide; it can influence the electric charge of cells and the adhesiveness of the cells. As was observed in one xanthan fermentation study, the zeta potential of cells remained constant during the initial growth phase and then increased its negative value during the production phase. They also found that the zeta potential of cells decreased from −34 mV at zero xanthan concentration to −74 mV at 0.1 g/L xanthan gum. The large change in zeta potential or increase in cell surface charges caused by the xanthan gum present in the fermentation broth should increase cell adsorption. It is clear in the present invention that the xanthan gum present in the fermentation broth contributed to the ability of cells to adsorb to fibers. As can be seen in Table 1, the adsorption rate constant, $k_a$, was much greater when xanthan gum was present in the broth. The total amounts of cells adsorbed to fibers were also much greater in the presence of xanthan gum. Without xanthan gum, the ability of cells to adsorb to fibers was poor. In fact, without xanthan gum, ~80% of the adsorbed cells could be easily desorbed from the fiber by pumping water through the fibrous bed (data not shown). With xanthan gum, vigorous washing of the fibrous materials with water was required to remove the adsorbed cells from the fiber.

FIG. 6 shows the scanning electronic micrographs of *X. campestris* cells adsorbed on the cotton fiber surface. As is seen in these photographs, cells were well dispersed on the fiber surface as a monolayer; they adsorbed on the surface mainly as individual cells without forming large cell clumps or aggregates. As can be seen in these SEM photographs, the fiber surface was rough and was also heavily covered with thin filamentous material, which had similar structures and dimensions to those reported for xanthan molecules. These SEM photographs prove that xanthan gum indeed has helped cell adsorption to the fiber surface.

The removal of cells from the xanthan fermentation broth by cell adsorption to various woven fibrous materials was accomplished. It was found that both cotton and polyester fibers could be used to adsorb *Xanthomonas campestris* cells present in the fermentation broth either during batch fermentation or after the fermentation. Almost all cells were removed from the fermentation broth by adsorption to fibers. Cotton terry cloth had rough surfaces and was the preferred material for cell adsorption, as cell adsorption to cotton was faster than to polyester fibers. The adsorption kinetics can be modeled by a first-order rate equation. The adsorption rate constants were 30–40% higher for cotton than for polyester. Cell adsorption was not efficient in the absence of xanthan gum, suggesting that the exopolysaccharide, xanthan gum, was important for efficient cell adsorption to fibers.

EXAMPLE 2

Xanthan Gum Fermentation by *Xanthomonas campestris* Immobilized in a Novel Centrifugal Fibrous-Bed Bioreactor The following Example shows the use of a method making and using a fibrous bed reactor for fermentation using immobilized cells in accordance with one embodiment of the present invention.

In this embodiment of the present invention, a centrifugal fibrous-bed bioreactor was constructed and used for viscous xanthan gum fermentation. The feasibility and performance of a rotating fibrous-bed bioreactor for long-term production of cell-free xanthan gum broth is shown in repeated batch mode. The effects of rotational speed of the fibrous bed on oxygen transfer rate and xanthan production rate in the bioreactor were also demonstrated. A comparison between the performance of the reactor and that of a conventional stirred tank fermentor was made, and the effect of glucose (i.e., the carbon source) to yeast extract (i.e., the nitrogen source) ratio in the fermentation medium on xanthan production rate and yield are also reported.

Materials and Methods

Culture and Media

*Xanthomonas campestris* NRRL B-1459 was obtained from the Northern Regional Research Laboratory (NRRL) of the U.S. Department of Agriculture (Peoria, Ill.). Stock cultures of *X. campestris* NRRL B-1459 were maintained on agar slants, which contained 10 g/L glucose, 3 g/L yeast extract, 5 g/L peptone, and 15 g/L agar, and were stored at 4° C. The culture was transferred once every two weeks to maintain good viability and stability for xanthan production. Actively growing cells from a newly prepared slant culture (about 24–36 hour incubation time at 30° C.) were inoculated into 500-mL Erlenmeyer flasks containing 100 mL liquid medium. After incubation for 24 hours at 30° C. in an incubator-shaker, the 100-mL liquid culture was used to inoculate the fermentor containing 5 L of the medium.

Unless otherwise noted, the medium used in fermentation study consisted of 25 g/L glucose, 3 g/L yeast extract (USB, Cleveland, Ohio), 2 g/L $K_2HPO_4$, 0.1 g/L $MgSO_4 \times 7H_2O$, a 500 ppm (v/v) antifoam A (Sigma Chemicals). Tap water was used in preparing the medium to provide trace elements. The medium was prepared in two parts; the first part contained all the basic medium components except for glucose, and the second part was a concentrated glucose solution. The initial medium pH was adjusted to 7 by adding 4N HCl. These two solutions were autoclaved at 121° C. and 15 psig for 25 min., allowed to cool to room temperature, and then mixed together aseptically.

Construction of Centrifugal, Packed-Bed Bioreactor (CPBR)

The centrifugal, packed-bed bioreactor was constructed using a 5-L fermentor (BioFlo II, New Brunswick Scientific Co., Edison, N.J.) with the immobilized-cell matrix contained in a support container attached to the central spinning shaft of the fermentor impeller (see FIG. 7). The support container was a cylindrical cup (9 cm in diameter and 15 cm in height) with a central hollow core (2.7 cm in diameter), made of stainless steel plate with 3/16" round perforations (Small Parts, Miami, Fla.). A selected fibrous sheet matrix (100% cotton towel; 5 mm×15 cm×80 cm) was overlaid with a crimped stainless steel wire cloth of the same dimension (Goodloe, Glitch Technology Corp., Dallas, Tex.), spirally wound around the vertical axis, and packed in the support container. The packed volume was ~850 mL. Four tilted exterior baffles mounted on the wall of the container caused a downloop flow pattern when the cup was rotated counter-clockwise. A disk-blade turbine impeller installed at ~1.5 cm below the cup provided turbulent mixing for the bottom part of the fluid in the fermentor. The centrifugal force generated from rotating the cup removed xanthan gum from the immobilized-cell matrix and moved it to the outer bulk broth. Broth was pumped from the bottom of the reactor vessel back into the center top of the rotating cup by a high-speed peristaltic pump (Masterflex with No. 24 pump head, Cole-Parmer, Chicago, Ill.) at a flow rate of ~270 mL/min. This recirculation stream was sprayed onto the rotating fibrous matrix through a nozzle.

Sterile air was introduced into the medium through a ring sparger at the bottom of the fermentor vessel. Unless otherwise noted, the aeration rate was controlled at 1.5 vvm. The temperature was controlled at 30±0.1° C. The reactor pH value was maintained at 7.0±0.1 by adding 2.0 N potassium hydroxide. The dissolved oxygen tension in the broth was monitored by using a dissolved oxygen probe and analyzer (New Brunswick Scientific, DO-40), which was connected to a chart recorder (LINSEIS L-4000 Digital Flatbed Recorder) to record dissolved oxygen tension profiles.

Bioreactor Startup and Cell Immobilization

The bioreactor was autoclaved twice at 121° C., 15 psig for 30 minutes and then filled with 5 liter sterile media containing 25 g/L glucose and 3 g/L yeast extract, and then inoculated with 100 mL flask culture. Unless otherwise noted, the cells in the bioreactor were first grown at pH 6 and 23° C., the optimal conditions for cell growth. The bioreactor was aerated at a volumetric flow rate of 5.0 std. liter/min. During this period, the reactor impeller and the fibrous matrix were spun at 150 rpm to provide good mixing. Then, when the reactor reached its highest cell density at ~24 hours, the fermentation conditions were changed to pH 7, 30° C., and 350 rpm to promote xanthan production and cell immobilization. The fermentation broth was then harvested at ~50 hours when all glucose in the medium had been consumed and by that time all cells had also been immobilized onto the fibrous matrix.

Repeated Batch Fermentation

After the first batch fermentation, the bioreactor was operated as a repeated batch system. The viscous broth was replaced with new sterile medium at the end of each batch fermentation, as determined from the alkali addition rate approaching zero. New medium for next batch fermentation was prepared in advance and pumped into the bioreactor at a flow rate of ~200 mL/min. immediately after all xanthan broth had been pumped out of the bioreactor, which took about 25 minutes. The batch fermentation was repeated several times with 25 g/L glucose medium and then with 50 g/L glucose medium to study the effect of C/N ratio on xanthan production.

The CPBR performance was studied under either liquid-continuous mode, where the fibrous bed was completely immersed in 5 L media, or gas-continuous mode, where 90% of the fibrous bed was exposed to air with only 2.5 L media in the fermentor vessel. The first study was conducted in liquid-continuous mode (5 L media) and 150 rpm rotational speed. The second study was also in the liquid-continuous mode, but at 350 rpm rotational speed, the highest rotational speed that could be used with the present equipment without causing severe vibration of the rotating shaft. The third study was conducted in gas-continuous mode (2.5 L media) and at 350 rpm.

Samples of the fermentation broth were taken at proper time intervals. The cell density in the sample was determined immediately by measuring the optical density of the cell suspension. The sample was then frozen and stored for future analysis of glucose and xanthan concentrations. The quality of xanthan produced from each batch was also determined by measuring the apparent viscosity of the xanthan broth at a selected xanthan concentration of 18 g/L using a Brookfield viscometer.

Determination of Immobilized Cell Density

The immobilized cell density in the bioreactor was estimated at the end of each bioreactor study. First, all liquid in the bioreactor was drained, and the liquid volume and OD were measured to estimate the total suspended cells (cells in the free solution) present in the reactor. In this study, however, no cells were found in the liquid medium. The drained fibrous matrix was removed from the reactor and washed several times with water until almost all cells had been removed. The total volume of the washing water and its OD, as well as its dry weight, were measured and used to estimate the total amount of cells immobilized in the fibrous matrix.

Determination of Cell Viability

The relative viability of immobilized cells as compared to free cells was determined by a plate count method. Small pieces of fibrous samples were cut off from the fibrous matrix and placed in test tubes containing sterile water. The immobilized cells in the fibrous matrix were then washed off from the matrix by vortexing for ~3 minutes. One mL of the cell suspension sample was then subjected to serial dilutions with saline before transferred onto agar plates. The total viable cell number was determined from the colony count (between 30–300) times the dilution factor used in preparing the sample. Meanwhile, the OD of the cell suspension was also measured to estimate the total cell number in the sample using a standard correlation between OD and total cell number obtained using actively growing free cells in shake flasks (24 hours old), which should have 100% viability (i.e., viable cell number=total cell number). A linear relationship between the plate count number (which was assumed to be equal to the total cell number) and OD reading was obtained from the free cell sample and was used as the standard correlation. The viability of immobilized cells was then determined from the ratio of the total viable cell number determined from the plate count to the total cell number determined from the measured OD value.

Scanning Electron Microscopy

Several small pieces of the fibrous material were taken as samples from the drained fibrous matrix. These samples were immersed in 2.5% glutaraldehyde solution overnight and then rinsed completely with double distilled water, approximately 10 times for 15 minutes each. The samples were then gradually dehydrated with 20%–70% ethanol in increments of 10% by holding the samples at each concentration for 30 min. The partially dehydrated samples were left in 70% ethanol overnight, then dehydrated further with 80% ethanol once and twice with 95% and 100% ethanol for 30 minutes each time. These samples were then cryogenically dried at critical point with liquid $CO_2$. All steps, except for the critical drying, were carried out at 4° C. The completely dried samples were coated with gold/palladium before taking SEM photographs using the JOEL model 820 SEM.

Analytical Methods

Cell Density

Samples of fermentation broth were collected into centrifuge tubes. Depending on the broth viscosity, the broth samples were diluted with tap water by a factor of two to six, and the diluted solutions were centrifuged at 12,000 rpm (16,000×g) for 30 minutes at 5° C. to precipitate the suspended cells. Cells were then re-suspended in water and the optical density at 650 nm ($OD_{650}$) was measured using a spectrophotometer. The OD readings were then compared to a standard correlation between OD and cell density (g/L). The cell density was proportional to OD when the optical density was below 0.5, with one unit of OD equaling to 0.4 g/L cell. The total cell dry weight in the cell suspension was also determined after drying at 105° C. for ~7 hours in a vacuum oven. The dry weight measurement was duplicated to reduce the experimental errors to within 0.2%.

Glucose Concentration

The glucose concentration was determined by using a glucose analyzer (YSI Model 2700 SELECT, detection range: 0–25 g/L). Properly diluted cell-free samples were presented to the needle port for automatic sample injection (adjustable from 5 to 65 microliters). The analysis is based on a biosensor membrane with immobilized glucose oxidase.

Xanthan Gum Concentration

Xanthan concentration in the fermentation broth was estimated from the broth viscosity with proper dilution. The viscosity of the cell-free fermentation broth was measured with a Brookfield viscometer (RVTD II) using spindle No. 1 at 100 rpm. The viscosity was then compared to a standard correlation between the viscosity and the xanthan concentration (g/L), which was linear when xanthan concentration was below 0.6 g/L. Samples were diluted with water to the proper concentration range before viscosity was measured, using known procedures. The final xanthan concentration of each batch fermentation was also determined by measuring the total dry weight of xanthan gum in the fermentation broth after purification by alcohol precipitation. The xanthan dry weight measurement was also used to verify the xanthan concentration determined from viscosity.

Results and Discussion
CPBR Reactor Startup

Typical kinetics of cell growth and xanthan production in the centrifugal, packed-bed bioreactor during reactor startup is shown in FIG. 8. Exponential cell growth, but small amounts of xanthan biosynthesis, occurred during the initial 24 hour period, which is also typical of xanthan gum batch fermentation with free cells. However, at ~24 hours when the culture reached the stationary phase, the cell density in the fermentation broth rapidly decreased while xanthan production continued to increase, indicating that the cells were immobilized (adsorbed) onto the matrix. All suspended cells disappeared and were immobilized onto the fibrous matrix by 50 hours, as indicated by the broth optical density of being zero. No free cells were detected in the subsequent repeated batch fermentations, indicating that all cells, both existing and newly grown, remained immobilized on the fibrous matrix. With all cells immobilized in the fibrous matrix, a cell-free xanthan broth was produced. The reactor pH was changed from 6.0 to 7.0 and temperature from 23° C. to 30° C. at 24 hours when the cell growth reached a maximum value to promote xanthan production and cell immobilization.

Liquid-Continuous Fermentation (CPBR-LC)

FIG. 9 shows the kinetics for four repeated batch fermentations at the low rotational speed of 150 rpm. In the first two batches, the xanthan production rate remained almost unchanged, whereas the following two batches showed declined production rates. FIG. 9b shows that both xanthan yield ($Y_{p/s}$) and volumetric xanthan productivity (dP/dt) were lower for the last two batches. The reduced xanthan production in the later two batches was caused by oxygen limitation in the system and possibly a low cell viability at the low rotational speed used in the fermentation. Agitation and aeration were relatively poor at 150 rpm when the xanthan concentration was higher than 1%.

Figure 10:
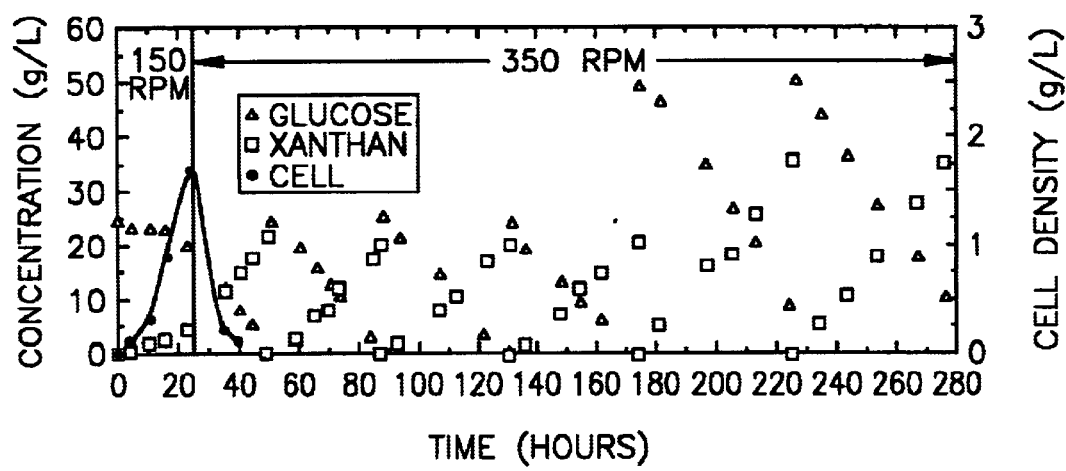
FIG. 10 shows a graph of concentration/cell density vs. time showing fermentation time course data for repeated batch xanthan fermentations with a CPBR at 350 rpm rotational speed for the fibrous bed under liquid continuous condition (CPBR-LC), in accordance with one embodiment of the present invention.
Figure 11:
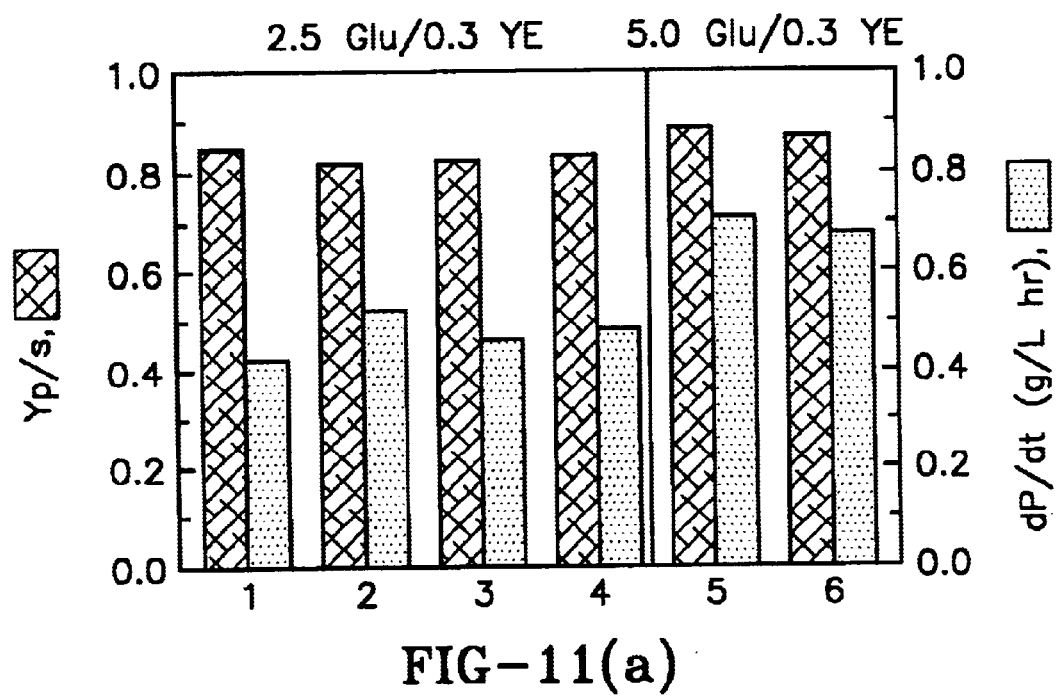
FIG. 11 shows two graphs pertaining to repeated batch xanthan fermentations with CPBR-LC at 350 rpm rotational speed: (a) a plot of xanthan gum yield and volumetric productivity, and (b) a plot of measured broth viscosity at 1.8% xanthan concentration, in accordance with one embodiment of the present invention.
Figure 11:
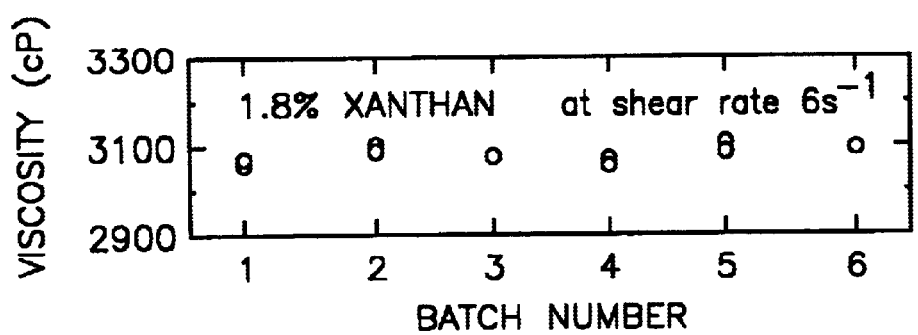

To improve oxygen transfer and CPBR performance, the rotational speed was increased to 350 rpm after cells were immobilized onto the matrix. As shown in FIG. 10, the fermentation time required for each batch at this rotational speed was much shorter than that at 150 rpm. The fermentation time to reach ~2.5% xanthan concentration was reduced to ~40 hours, as compared to 50 hours or longer for the conventional batch fermentation process. The productivity of the immobilized cells on the matrix was evaluated for long term operation by extending the repeated batch cycles. The reactor showed stable and consistent results for all six consecutive batches studied. As shown in FIG. 11, the xanthan yield remained at ~85% and the quality of xanthan polymers produced, as determined by the solution viscosity of 1.8% xanthan concentration, remained unchanged for all six batches. The experiment was stopped because the reactor was contaminated by mold at the end of the last batch. The reactor productivity reached ~0.7 g/L×h, which was significantly higher than that of the conventional batch xanthan fermentation (~0.5 g/L×h). The immobilized cells in the CPBR thus can be repeatedly used for xanthan production for a long period.

It is clear that cell immobilization using fibrous matrix as the carrier can produce cell-free xanthan broth at high production rate. After the cells were successfully immobilized, they became available for reuse in subsequent batches, thus eliminating the long period (~24 hours) for cell growth required in the conventional batch fermentation. Production of xanthan gum by repeated batch fermentations with free cells has also been demonstrated with good stability for three consecutive cycles. However, in these studies 20% of the fermentation broth was retained as inocula for new batch cycle and 50 hours were required to reach 2% xanthan concentration in each cycle. With cell immobilization, there is no need to retain any fermentation broth for the new batch cycle, thus greatly enhancing process productivity.

Gas-Continuous Fermentation (CPBR-GC)

Since all cells were immobilized in the fibrous matrix, xanthan gum production could only take place when the glucose medium was in contact with the fibrous matrix. The fermentation time thus should be further reduced by increasing the liquid-cell contact. Since it was difficult to increase the recirculation pump speed in the experiment, the total liquid volume in the reactor vessel was reduced to half. This not only would increase the contact frequency between cells and the liquid medium, it also increased the effective cell concentration per liter liquid medium in the reactor and mass transfer between liquid and air.

Figure 12:
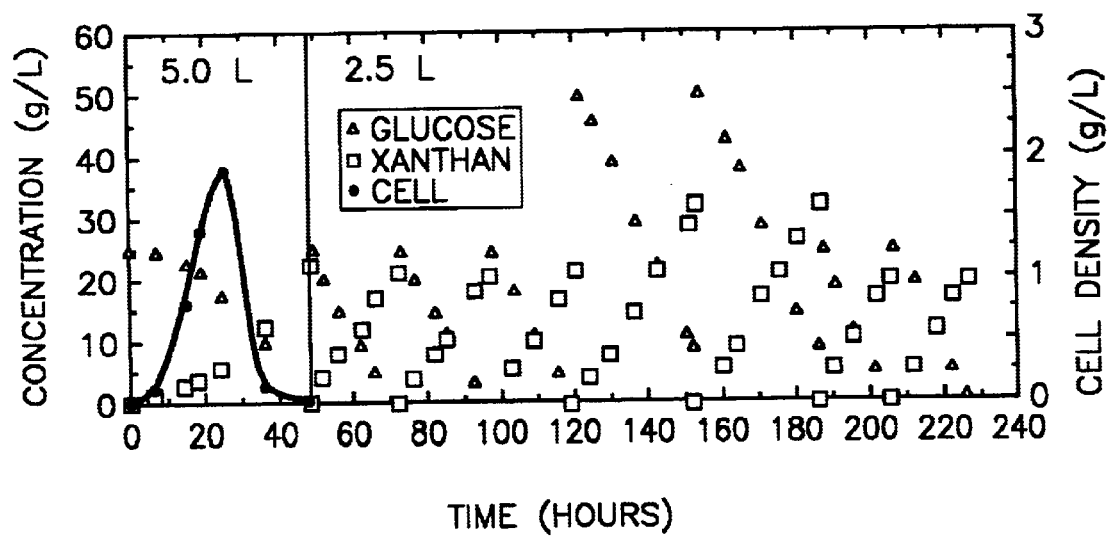
FIG. 12 shows a graph of concentration/cell density vs. time as fermentation time course data for repeated batch xanthan fermentations with CPBR at 350 rpm rotational speed for the fibrous bed under gas continuous condition (CPBR-GC), in accordance with one embodiment of the present invention.

FIG. 12 shows the fermentation results from gas-continuous operation with 2.5 liters media in the fermentor vessel. As expected, the fermentation time for each batch cycle was dramatically reduced to 24–26 hours or about half of the time required for the conventional process. The xanthan yield, volumetric xanthan productivity, and xanthan quality from eight consecutive batches are shown in FIG. 13. The volumetric productivity was ~1 g/L×h based on the total liquid volume in the fermentor vessel, and ~3 g/L×h based on the packing volume (the volume occupied by the rotating fibrous matrix). The productivity can be further increased by increasing the medium recirculation rate, which increases gas-liquid and cell-liquid contacts in the fibrous matrix. The oxygen transfer rate can also be enhanced by increasing liquid recirculation rate and the rotational speed of the fibrous bed. This should result in an even higher xanthan production rate.

Immobilized Cell Density

Figure 14:
FIG. 14 shows a scanning electron micrograph of adsorption of *Xanthomonas campestris* on a fiber surface.

Fibrous samples from various parts of the fibrous matrix were examined for cell density distribution at the end of each reactor study. It was found that cells were evenly distributed onto the fibrous matrix. FIG. 14 shows the attachment of *Xanthomonas campestris* on the fiber surface. The immobilized cells were well spread on the fiber surface. They adsorbed on the surface mainly as individual cells without forming large cell clumps or aggregates.

At the end of each reactor study, the amount of immobilized cells in the bioreactor was determined and was found to be 34 g for the liquid continuous reactor and 38.4 g for the gas-continuous reactor. This gave equivalent liquid cell densities of 6.8 g/L and 15.36 g/L, respectively, which were at least three to seven times that obtained in the conventional free-cell batch xanthan fermentation (<~2 g/L). It is clear that the high immobilized cell density contributed to high productivity for CPBR. However, the increase in CPBR productivity was less proportional to the increase in the total cell density. The cell viability of the immobilized cells in the CPBR at the end of the study was only ~60% of that for free, suspended cells. This explained partially why the volumetric xanthan productivity of CPBR was not proportional to the total cell density in the bioreactor.

Comparison between STR and CPBR

Figure 16:
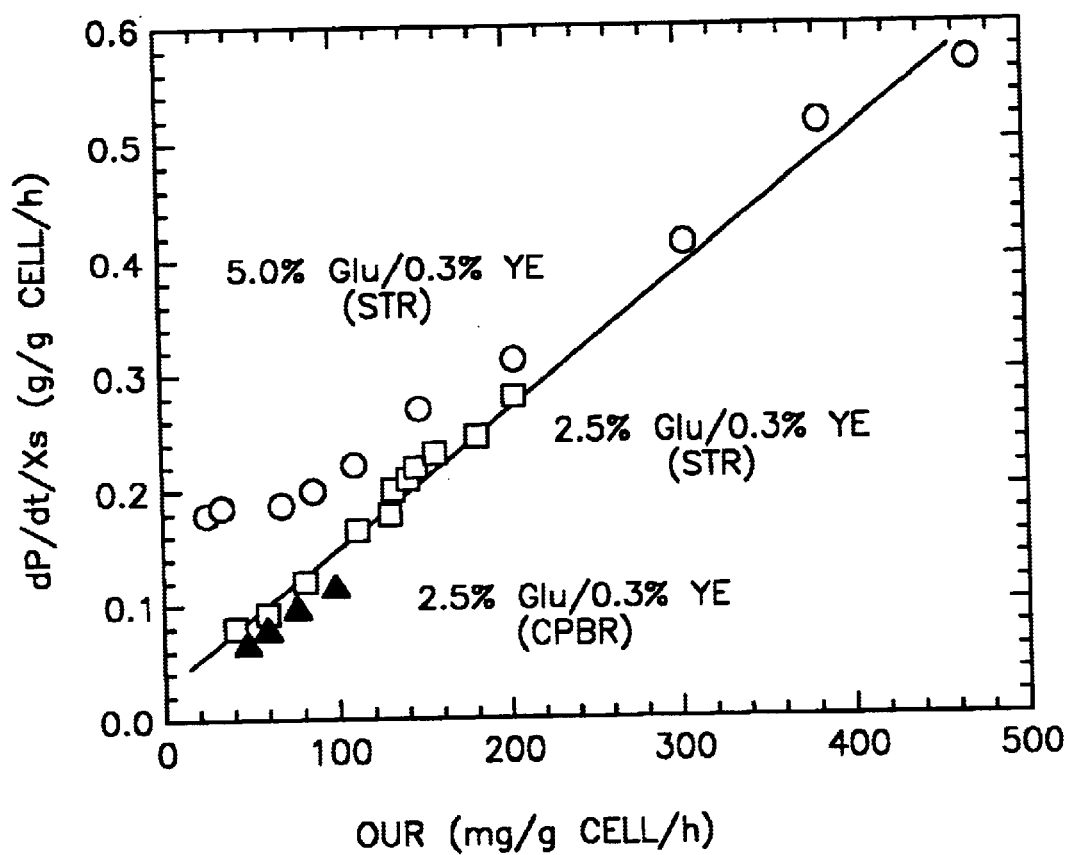
FIG. 16 shows a graph of specific xanthan productivity (dP/dt/Xs) as a linear function of specific oxygen uptake rate (OUR) during batch xanthan gum fermentations.

For comparison purposes, batch xanthan fermentations with free cells in conventional stirred tank bioreactor (STR) were also studied at 30° C. and pH 7.0. Compared to the CPBR results, the fermentation time with STR was long: ~70 hours for fermentation with 2.5% glucose medium and ~120 hours with 5.0% glucose medium. FIG. 15 shows the comparison of volumetric xanthan productivities (dP/dt) and specific xanthan productivities ($dP/dt/X_s$) from STR, CPBR-LC, and CPBR-GC. The specific productivity was estimated from the volumetric productivity divided by the final cell density in the bioreactor ($X_s$). As can be seen in FIG. 16, CPBR gave higher volumetric productivity than conventional STR, mainly because of its higher cell density in the reactor. However, CPBR had a lower specific productivity (FIG. 15*b*) because of the relatively low cell viability, only ~60% at the end of the study. Some cells might have died due to starvation during medium change-over between batch runs. However, the low specific productivity also indicated that the oxygen transfer rate in the CPBR might not be high enough and thus must be further increased in order to fully utilize the high density of immobilized cells in the fibrous matrix.

Effect of Oxygen Uptake Rate

The dissolved oxygen tension (DOT) in the fermentation broth generally decreased as the fermentation progressed, dropping gradually from 100% to ca. 50% during growth phase. As the broth became more viscous at 2%~3% xanthan, DOT dropped quickly down to below 10%. The DOT must be maintained above 20% to prevent any adverse effect on xanthan production caused by oxygen limitation. Oxygen transfer rate has been found to have profound effects on both specific xanthan production rate and the molecular weight of the xanthan product from fermentation. The oxygen transfer rate (OTR) during the batch fermentation can be estimated from the measured DOT and the overall mass transfer coefficient, $k_L a$, and the solubility of oxygen in xanthan broth. As was observed in practice of the present invention (data not shown), as the xanthan concentration increased, OTR, specific oxygen uptake rate (OUR), and specific xanthan productivity all decreased. There was a strong correlation between specific OUR and specific xanthan productivity. As shown in FIG. 16, the specific xanthan productivity was proportional to the specific oxygen uptake rate during xanthan gum fermentation, regardless of the bioreactor system used in the fermentation. Compared to STR, CPBR had relatively low specific OUR. Thus, the low specific xanthan productivity from CPBR can be attributed to the low specific oxygen uptake rate or OTR. The performance of CPBR thus can be further improved by increasing OTR in CPBR. This can be accomplished by increasing the liquid recirculation rate and the rotational speed of the fibrous matrix. The mass transfer rate between gas and liquid can be greatly enhanced by increasing their contact, which can be accomplished without incurring flooding under high gravitational force.

Effect of C/N Ratio

In batch fermentation, it took ~24 hours for cells to reach a maximum cell density with the low glucose (e.g. 2.5%) medium. Large amounts of xanthan began to be produced when cell growth stopped. On the contrary, for the high glucose medium (5.0%), cell growth was much slower and was in parallel with xanthan formation for most of the fermentation time (data not shown). Both the cell yield and specific growth rate of *X. campestris* in the stirred tank reactor (STR) were found to decrease with increasing C/N (glucose to yeast extract) ratio in the medium. On the other hand, the xanthan yield and specific xanthan production rate increased with increasing C/N ratio in the medium. Similarly, it was also found with CPBR that the volumetric xanthan productivity was significantly higher with the medium with a higher C/N ratio (FIG. 15). As can also be seen from FIG. 13, both the xanthan yield and volumetric xanthan productivity were about the same for fermentations with 5.0% glucose/0.3% yeast extract and 2.5% glucose/0.15% yeast extract. Thus, the enhanced xanthan production rate at the higher C/N ratio also was achieved at a relatively low yeast extract concentration. This clearly showed that C/N ratio, instead of yeast extract or glucose concentration, was the major factor in affecting the xanthan gum production rate by the immobilized cells.

Conclusion

The centrifugal packed-bed bioreactor of the present invention was able to produce xanthan gum at a productivity of twice that for the present industrial process. The intimate air, liquid, and cell contact achieved via passing liquid medium and air through the porous fibrous matrix enhanced the oxygen transfer rate and allowed high cell density and xanthan productivity. The immobilized cells were able to be repeatedly used for xanthan fermentation to achieve stable, semi-continuous production of cell-free xanthan broth, as demonstrated in repeated batch mode for more than 8 batch cycles in this study. In principle, as long as the cells are able to be maintained at a high viability level, the production of xanthan gum could continue. Even with reduced viability, the high cell numbers present in the fibrous matrix can more than compensate for the problem. Cell density as high as 30 to 100 g/L has been attained with the fibrous bed bioreactor. The immobilized cell density in the CPBR can thus be increased several fold to further increase the reactor productivity if the oxygen transfer rate in the fibrous bed can also be increased.

Moreover, fermentation conditions can be easily shifted from growth-oriented for reactor startup to production-oriented for the following production period. The productivity of xanthan polymers can thus be further optimized in the immobilized cell bioreactor. Xanthan gum is produced as a secondary metabolite and its production is usually non-growth associated. The optimal conditions for cell growth and xanthan biosynthesis are known to be quite different. In general, optimal cell growth requires a relatively low temperature, 22 to 24° C., a pH of 6 or lower, and a low C/N ratio in the medium; whereas a higher temperature, 31 to 33° C., neutral pH, and a higher C/N ratio are needed for optimal xanthan production. Therefore, separation of cell growth and xanthan production into two stages should improve xanthan fermentation with enhanced cell growth as well as xanthan production. Such a two-step fermentation process can be easily carried out with the present immobilized cell bioreactor.

Accordingly, the present invention may include a process for separating cells from a cellular reaction media, which is mediated through the presence of a microbial polysaccharide (which may be added or be produced through the cellular reaction). The present invention also includes a cellular reaction method in a liquid media that may use the inventive separation process to remove cells.

The present invention also includes a method for conducting a cellular reaction in a liquid media which uses microbial polysaccharide-mediated or -enhanced attachment of cells to a fibrous material matrix. The invention also includes an apparatus for carrying out such a method.

In view of the foregoing disclosure, it may become apparent to one of ordinary skill in the art to make modifications to the present invention, such as through substitution of equivalent materials and process steps, without departing from the spirit of the invention as reflected in the appended claims.

What is claimed is:

1. An apparatus for separating microbial cells from a liquid containing said microbial cells, said apparatus comprising:

(a) a matrix of a fibrous material treated with at least one microbial polysaccharide; and (b) a liquid circulator device for circulating said liquid through said matrix of said fibrous material, such that said microbial cells are attached to said matrix of a fibrous material, said attachment mediated by said at least one microbial polysaccharide.

2. An apparatus for facilitating a method for producing at least one cellular reaction product from at least one substrate substance in a liquid, said apparatus comprising:

(a) a matrix of a fibrous material having an interior and an outer surface, said fibrous material treated with at least one microbial polysaccharide and having adsorbed thereupon microbial cells of a microorganism capable of converting said at least one substrate substance to said at least one cellular reaction product wherein said adsorption of said microorganisms to said matrix is mediated by said at least one microbial polysaccharide; and (b) a liquid circulator device for circulating said liquid through said matrix of said fibrous material.

3. An apparatus for separating microbial cells from a liquid containing said microbial cells, or for facilitating a method for producing a cellular reaction product in a liquid, said apparatus comprising:

(a) a matrix of a fibrous material treated with at least one microbial polysaccharide, and having an interior and an outer surface;

(b) liquid application dispenser for dispensing said liquid into said interior of said matrix of said fibrous material such that said microbial cells are attached to said matrix of a fibrous material, said attachment mediated by said at least one microbial polysaccharide; and (c) a spinner adapted to spin said matrix of said fibrous material such that said liquid, once in said interior of said matrix of said fibrous material, moves out of said outer surface of said matrix of said fibrous material.

4. An apparatus according to claim 3, said apparatus additionally comprising a recirculator adapted to recirculate liquid moving out of said outer surface of said matrix of said fibrous material into said interior of said matrix of said fibrous material.

5. An apparatus according to claim 3 wherein said at least one microbial polysaccharide is selected from the group consisting of xanthan, dextran, pullulan and mixtures thereof.

6. An apparatus according to claim 3 wherein said fibrous material is selected from the group consisting of looped cotton terry cloth, cotton fabric sheet cloth, 50% cotton-50% polyester fabric sheet cloth, and polyester fabric sheet cloth.

7. An apparatus according to claim 3 wherein said fibrous material is selected from the group consisting of looped cotton terry cloth and cotton fabric sheet cloth.

8. An apparatus for facilitating a method for producing at least one cellular reaction product from at least one substrate substance in a liquid, said apparatus comprising:

(a) a matrix of a fibrous material having an interior and an outer surface, said fibrous material treated with at least one microbial polysaccharide and having adsorbed thereupon microbial cells of a microorganism capable of converting said at least one substrate substance to said at least one cellular reaction product;

(b) liquid application dispenser for dispensing said liquid into said interior of said matrix of said fibrous material; and (c) a spinner adapted to spin said matrix of a fibrous material such that said liquid, once in said interior of said matrix of said fibrous material, moves through said matrix of a fibrous material toward said outer surface of said matrix of said fibrous material so as to bring said liquid in contact with said microbial cells of said microorganism.

9. An apparatus according to claim 8 additionally comprising a recirculator adapted to recirculate liquid moving out of said outer surface of said matrix of said fibrous material into said interior of said matrix of said fibrous material.

10. An apparatus according to claim 8 wherein said at least one microbial polysaccharide is selected from the group consisting of xanthan, dextran, pullulan and mixtures thereof.

11. An apparatus according to claim 8 wherein said fibrous material is selected from the group consisting of looped cotton terry cloth, cotton fabric sheet cloth, 50% cotton-50% polyester fabric sheet cloth, and polyester fabric sheet cloth.

12. An apparatus according to claim 8 wherein said fibrous material is selected from the group consisting of looped cotton terry cloth and cotton fabric sheet cloth.

13. An apparatus for facilitating a method for producing at least one cellular reaction product from at least one substrate substance in a liquid, said apparatus comprising:

(a) a matrix of a fibrous material having an interior and an outer surface, said fibrous material treated with at least one microbial polysaccharide and having adsorbed thereupon microbial cells of a microorganism capable of converting said at least one substrate substance to said at least one cellular reaction product;

(b) a reaction vessel for holding said liquid; and (c) a transport device adapted to move said matrix of said fibrous material and said liquid relative to one another.

14. An apparatus for facilitating a method for producing at least one reaction product from at least one substrate substance, in a liquid, said apparatus comprising:

(a) a liquid circulator device; and (b) a matrix of fibrous material disposed in said liquid circulator device, wherein said liquid circulator device circulates said liquid through said matrix of fibrous material, said liquid containing at least one microbial polysaccharide and microbial cells of a microorganism capable of converting said at least one substrate substance to said at least one reaction product, wherein adsorption of said microbial cells onto said matrix of fibrous material is mediated by said at least one microbial polysaccharide.

15. An apparatus for facilitating a method for producing at least one reaction product from at least one substrate substance, in a liquid, said apparatus comprising:

(a) a matrix of fibrous material;

(b) a reaction vessel for holding a liquid, said matrix of fibrous material disposed in said reaction vessel; and (c) a transport device adapted to move said matrix of said fibrous material and said liquid relative to one another, said liquid containing at least one microbial polysaccharide and microbial cells of a microorganism capable of converting said at least one substrate substance to said at least one reaction product, wherein adsorption of said microbial cells onto said matrix of fibrous material is mediated by said at least one microbial polysaccharide.

16. An apparatus for facilitating a method for producing at least one reaction product from at least one substrate substance, in a liquid, said apparatus comprising:
   (a) a matrix of fibrous material having an interior and an outer surface;
   (b) liquid application dispenser for dispensing said liquid into said interior of said matrix of fibrous material; and
   (c) a spinner adapted to spin said matrix of fibrous material such that said liquid, once in said interior of said matrix of fibrous material, moves through said matrix of fibrous material toward said outer surface of said matrix of fibrous material so as to bring said liquid in contact with microbial cells of a microorganism, wherein said liquid contains at least one microbial polysaccharide and microbial cells of a microorganism capable of converting said at least one substrate substance to said at least one reaction product, wherein adsorption of said microbial cells onto said matrix of fibrous material is mediated by said at least one microbial polysaccharide.

* * * * *

UNITED STATES PATENT AND TRADEMARK OFFICE
CERTIFICATE OF CORRECTION

PATENT NO.   : 6,787,340 B2
DATED        : September 7, 2004
INVENTOR(S)  : Yang It is certified that error appears in the above-identified patent and that said Letters Patent is hereby corrected as shown below:

Title page,
Item [73], Assignee, please delete "Columbia" and insert -- Columbus --.
Item [56], References Cited, OTHER PUBLICATIONS, please delete "Busscher, H. J.; Sjollema, J.; et al., Relative Importance of Surface Free Energy as a Measure of Hydrophobicity in Bacterial Adhesion to Solid Surfaces, pp. 355-359, 1990, Microbial Cell Surface Hydrophobicity." and insert -- Busscher, H. J.; Sjollema, J.; et al., Relative Importance of Surface Free Energy as a Measure of Hydrophobicity in Bacterial Adhesion to Solid Surfaces, pp. 335-359, 1990, Microbial Cell Surface Hydrophobicity. --

Column 1,
Line 13, please delete "6,003,896" and insert -- 6,033,896 --.

Column 2,
Line 52, please delete "form" and insert -- from --.

Column 3,
Line 7, please delete "cells-alive, dead or attenuated-and" and insert -- cells--alive, dead or attenuated -- and --.

Column 5,
Line 13, please delete "the outer surface" and insert -- the surface --.

Column 8,
Lines 55-56, please delete "30° C." and insert -- 30° C --.
Line 67, please delete "23° C.," and insert -- 23° C, --.

Column 9,
Line 4, please delete "30° C.," and insert -- 30° C, --.
Line 25, please delete "25° C." and insert -- 25° C --.
Line 47, please delete "5° C." and insert -- 5° C --.
Line 55, please delete "105° C." and insert -- 105° C --.

Column 13,
Line 65, please delete "30° C." and insert -- 30° C --.
Line 67, please delete "30° C." and insert -- 30° C --.

UNITED STATES PATENT AND TRADEMARK OFFICE
CERTIFICATE OF CORRECTION

PATENT NO. : 6,787,340 B2
DATED : September 7, 2004
INVENTOR(S) : Yang

It is certified that error appears in the above-identified patent and that said Letters Patent is hereby corrected as shown below:

Column 14,
Line 5, please delete "a" and insert -- and --.
Line 12, please delete "121° C." and insert -- 121° C --.
Line 56, please delete "121° C.," and insert -- 121° C, --.
Line 61, please delete "23° C.," and insert -- 23° C, --.
Line 67, please delete "30° C.," and insert -- 30° C, --.

Column 16,
Line 33, please delete "5° C." and insert -- 5° C --.
Line 35, please delete "($OD_{650}$,)" and insert -- ($OD_{650}$) --.
Line 41, please delete "105° C." and insert -- 105° C --.

Column 17,
Lines 20-21, please delete "23° C. to 30° C. " and insert -- 23° C to 30° C --

Column 18,
Line 63, please delete "30° C." and insert -- 30° C --.

Column 20,
Line 37, please delete "22 to 24° C.," and insert -- 22 to 24° C, --.
Lines 38-39, please delete "31 to 33° C.," and insert -- 31 to 33° C, --.

Signed and Sealed this

Seventh Day of December, 2004

JON W. DUDAS
*Director of the United States Patent and Trademark Office*